US009982260B2

(12) United States Patent
Kendall et al.

(10) Patent No.: US 9,982,260 B2
(45) Date of Patent: May 29, 2018

(54) IDENTIFICATION OF STRUCTURALLY SIMILAR SMALL MOLECULES THAT ENHANCE THERAPEUTIC EXON SKIPPING

(71) Applicant: The Regents of the University of California, Oakland, CA (US)

(72) Inventors: Genevieve C. Kendall, Los Angeles, CA (US); Stanley F. Nelson, Los Angeles, CA (US); M. Carrie Miceli, Los Angeles, CA (US)

(73) Assignee: The Regents of The University of California, Oakland, CA (US)

( * ) Notice: Subject to any disclaimer, the term of this patent is extended or adjusted under 35 U.S.C. 154(b) by 0 days. days.

(21) Appl. No.: 15/025,952

(22) PCT Filed: Sep. 30, 2014

(86) PCT No.: PCT/US2014/058436
§ 371 (c)(1),
(2) Date: Mar. 30, 2016

(87) PCT Pub. No.: WO2015/048792
PCT Pub. Date: Apr. 2, 2015

(65) Prior Publication Data
US 2016/0257952 A1  Sep. 8, 2016

Related U.S. Application Data

(60) Provisional application No. 61/884,671, filed on Sep. 30, 2013.

(51) Int. Cl.
| | | |
|---|---|---|
| *A61K 31/4745* | (2006.01) | |
| *A61K 31/475* | (2006.01) | |
| *A61K 31/496* | (2006.01) | |
| *A61K 31/5415* | (2006.01) | |
| *A61K 31/7088* | (2006.01) | |
| *C12N 15/113* | (2010.01) | |
| *A61K 45/06* | (2006.01) | |

(52) U.S. Cl.
CPC .......... *C12N 15/113* (2013.01); *A61K 31/475* (2013.01); *A61K 31/4745* (2013.01); *A61K 31/496* (2013.01); *A61K 31/5415* (2013.01); *A61K 31/7088* (2013.01); *A61K 45/06* (2013.01); *C12N 2310/11* (2013.01); *C12N 2310/346* (2013.01); *C12N 2320/31* (2013.01)

(58) Field of Classification Search
None
See application file for complete search history.

(56) References Cited

U.S. PATENT DOCUMENTS 7,470,703 B1 * 12/2008 Miller ................. C07D 471/16
435/7.2

FOREIGN PATENT DOCUMENTS

WO  WO 2013/033407  3/2013

OTHER PUBLICATIONS

Al-Shanti, Nasser, Claire E. Stewart (2009). "Ca$^{2+}$/calmodulin-dependent transcriptional pathways: potential mediators of skeletal muscle growth and development." *Biological Reviews* 84: 637-652.
Andersson DC, Marks AR (2010) Fixing ryanodine receptor Ca leak—a novel therapeutic strategy for contractile failure in heart and skeletal muscle. Drug Discov Today Dis Mech 7: e151-e157.
Bellinger, et al. (2009) Hypernitrosylated ryanodine receptor calcium release channels are leaky in dystrophic muscle. Nat Med 15: 325-330.
Brown RD, Martin YC (1996) Use of Structure-Activity Data to Compare Structure-Based Clustering Methods and Descriptors for Use in Compound Selection. J Chem Inf Comput Sci 36: 572-584.
Cao Y, Charisi A, Cheng LC, Jiang T, Girke T (2008) ChemmineR: a compound mining framework for R. Bioinformatics 24: 1733-1734.
Chin D, Means AR (2000) Calmodulin: a prototypical calcium sensor. Trends Cell Biol 10: 322-328.
Cirak et al., "Exon skipping and dystrophin restoration in patients with Duchenne muscular dystrophy after systemic phosphorodiamidate morpholino oligomer treatment: an open-label, phase 2, dose-escalation study", *The Lancet*, 378(9791): 595-605, 2011.
Cook WJ, Walter U, Walter MR (1994) Drug binding by calmodulin: crystal structure of a calmodulin-trifluoperazine complex. Biochemistry 33: 15259-15265.
Fill M, Copello JA (2002) Ryanodine receptor calcium release channels. Physiol Rev 82: 893-922.
Hu, et al. (2010) Guanine analogues enhance antisense oligonucleotide-induced exon skipping in dystrophin gene in vitro and in vivo. Mol Ther 18: 812-818.
International Search Report and Written Opinion issued in PCT/US2014/058436, dated Jan. 12, 2015.
Johnson MA, Maggioria GM (1990) Concepts and Applications of Molecular Similarity. New York: John Wiley & Sons. 393 p, Table of Contents Only.
Kendall, et al. (2012) Dantrolene enhances antisense-mediated exon skipping in human and mouse models of Duchenne muscular dystrophy. Sci Transl Med 4: 164ra160.
Kobayashi, et al. (2005) Dantrolene stabilizes domain interactions within the ryanodine receptor. J Biol Chem 280: 6580-6587.
Kubinyi, Hugo (1998). "Similarity and Dissimilarity: A Medicinal Chemist's View." *Perspectives in Drug Discovery and Design*: 225-252.

(Continued)

*Primary Examiner* — Richard A Schnizer
(74) *Attorney, Agent, or Firm* — Norton Rose Fulbright US LLP

(57) ABSTRACT

This invention relates, e.g., to a method for enhancing exon skipping in a pre-mRNA of interest, comprising contacting the pre-mRNA with an effective amount of a compound such as, for example, Perphenazine, Flupentixol DiHCl, Zuclopenthixol or Corynanthine HCl, or a compound which shares a similar 2-D structure and activity level with one of these compounds, or a pharmaceutically acceptable salt, hydrate, solvate, or isomer of the compound, and, optionally, with an antisense oligonucleotide that is specific for a splicing sequence in the pre-mRNA Methods for treating Duchenne muscular dystrophy (DMD) are disclosed.

20 Claims, 13 Drawing Sheets

(56) References Cited

OTHER PUBLICATIONS

Luby-Phelps K, Hori M, Phelps JM, Won D (1995) Ca(2+)-regulated dynamic compartmentalization of calmodulin in living smooth muscle cells. J Biol Chem 270: 21532-21538.

Mercuri et al., "Muscular dystrophies", *The Lancet*, 381(9869): 845-860, 2013.

Ming, et al. (2013) The small molecule Retro-1 enhances the pharmacological actions of antisense and splice switching oligonucleotides. Nucleic Acids Res 41: 3673-3687.

Morales A (2000) Yohimbine in erectile dysfunction: the facts. Int J Impot Res 12 Suppl 1: S70-74.

Nishida et al., "Chemical treatment enhances skipping of a mutated exon in the dystrophin gene", *Nat Commun*, 2(308): 1-8, 2011.

Noble ME, Endicott JA, Johnson LN (2004) Protein kinase inhibitors: insights into drug design from structure. Science 303: 1800-1805.

O'Leary, et al. (2009) Identification of small molecule and genetic modulators of AON-induced dystrophin exon skipping by high-throughput screening. PLoS One 4: e8348.

Qin J, Zima AV, Porta M, Blatter LA, Fill M (2009) Trifluoperazine: a ryanodine receptor agonist. Pflugers Arch 458: 643-651.

Rousseau E, Smith JS, Meissner G (1987) Ryanodine modifies conductance and gating behavior of single Ca2+ release channel. Am J Physiol 253: C364-368.

Vandonselaar M, Hickie RA, Quail JW, Delbaere LT (1994) Trifluoperazine-induced conformational change in Ca(2+)-calmodulin. Nat Struct Biol 1: 795-801.

Xie, Jiuyong, Douglas L. Black. (2001). "A CaMK IV responsive RNA element mediates depolarization-induced alternative splicing of ion channels." *Nature* 410: 936-939.

Extended European Search Report and Opinion for EP14847022, dated Apr. 4, 2017.

"eScholarship: Search Results". Retrieved from "http://escholarship.org/search?creator=Kendall, Genevieve Claire" on Mar. 23, 2017.

Hoffman et al., *The American Journal of Pathology* 179.1, 12-22 (2011).

Kendall, *Small Molecule Calcium Modulators Enhance Antisense-Targeted Exon Skipping on the DMD Gene*, 2013.

Kendall et al., "Dantrolene Enhances Antisense-Mediated Exon Skipping in Human and Mouse Models of Duchenne Muscular Dystrophy", Science Translational Medicine, vol. 4, No. 164, (2012), pp. 74-91.

Kendall, *Small Molecule Calcium Modulators Enhance Antisense-Targeted Exon Skipping on the DMD Gene*, Dissertation, University of California, 2013.

\* cited by examiner

SEQUENCE LISTING

```
<160> NUMBER OF SEQ ID NOS: 3

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aacuuccucu uuaacagaaa agcauac                                              27

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucaaggaaga uggcauuucu                                                      20
```

```
<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-FAM

<400> SEQUENCE: 3
ucaaggaaga uggcauuucu                                                   20
```

IDENTIFICATION OF STRUCTURALLY SIMILAR SMALL MOLECULES THAT ENHANCE THERAPEUTIC EXON SKIPPING

This application is a national phase application under 35 U.S.C. § 371 of International Application No. PCT/US2014/058436, filed Sep. 30, 2014, which claims the benefit of the filing date of U.S. Provisional Application No. 61/884,671, filed Sep. 30, 2013. The entire contents of each of the above-referenced disclosures are specifically incorporated herein by reference without disclaimer.

STATEMENT OF GOVERNMENT SUPPORT

This invention was made with Government support under W81XWH-05-1-0616, awarded by the U.S. Army, Medical Research and Materiel Command and AR058333, awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Sep. 30, 2014, is named 58086-372475_SL.txt and is 1,060 bytes in size.

BACKGROUND INFORMATION

Duchenne muscular dystrophy (DMD) is the most common childhood muscular dystrophy affecting 1/4,000 males worldwide [1]. DMD is caused by mutations in the X-linked DMD gene, which encodes dystrophin, a protein that when absent compromises sarcolemma stability [2-5]. Resulting consequences include a cyclical degeneration and regeneration process in which muscle satellite cells are continuously replacing damaged myofibers [6,7]. Skeletal muscle is further insulted by immune cells that scavenge necrotic tissue, adipose cells replacing dystrophic muscle and fibrosis [8-11]. This culminates in an environment in which skeletal and cardiac muscle is progressively rendered non-functional, leading to respiratory or cardiac complications, and patient death by the third decade of life [12,13]. To date, no FDA approved therapies directly address the underlying genetic defect. Corticosteroids can prolong ambulation for up to 3 years and improve patient quality of life, but are not curative [14,15].

Several potential DMD therapies are in pre-clinical development or ongoing clinical trials [16-19]. The most progressed therapy is antisense oligonucleotide (AO) targeted DMD exon skipping. Two AO chemical backbones, 2-O-methyl (2'OMe) and morpholino (PMO), are in Phase IIb and Phase III clinical trials and target an exonic splice enhancer (ESE) element to skip DMD exon 51, addressing 13% of all DMD mutations [20-24]. After weekly systemic administration in DMD patients AOs rescued dystrophin expression ranging from 0-15% or 47% of normal levels [21,25]. Based on data from transgenic mdx mice and allelic diseases, X-linked dilated cardiomyopathy and Becker muscular dystrophy, it is predicted that 20-30% of normal dystrophin levels may be required for a therapeutic benefit [26-28]. In addition, antisense based therapies have variable exon skipping efficiencies within the same muscle, across muscle types, and between patients and types of deletions indicating potential for improvements [21,23,29].

There are many strategies to address limitations of AO distribution and exon skipping efficacy in vivo [30-33]. The present inventors have focused on finding independent molecular agents that potentiate antisense based exon skipping. Their previous work identified dantrolene, an FDA approved drug that increased AO targeted exon skipping activity in a high-throughput screen (HTS), in human and mouse cell models, and in mdx mice treated with AO provided a functional benefit [33]. Dantrolene and other small molecule inhibitors of the Ryanodine Receptor (RyR1) also increased exon 51 skipping in a patient iDRM, suggesting this as the relevant molecular target. These studies were also published as PCT WO2013/033407, which is incorporated by reference herein in its entirety. This previous work highlights the advantage of a HTS workflow, which identifies compounds with significant biological activity and effectively re-purposes their use. The present inventors have focused in particular on identifying FDA approved drugs that modulated exon skipping activity, given that these drugs typically have known molecular targets and toxicity profiles.

There is a need to identify additional small molecules which potentiate AO exon skipping (e.g. in skeletal muscle), and to identify molecular targets and to better understand relevant pathways and interactions for small molecule potentiation of AO exon skipping in order to identify additional small molecules.

DESCRIPTION

Figure 1:
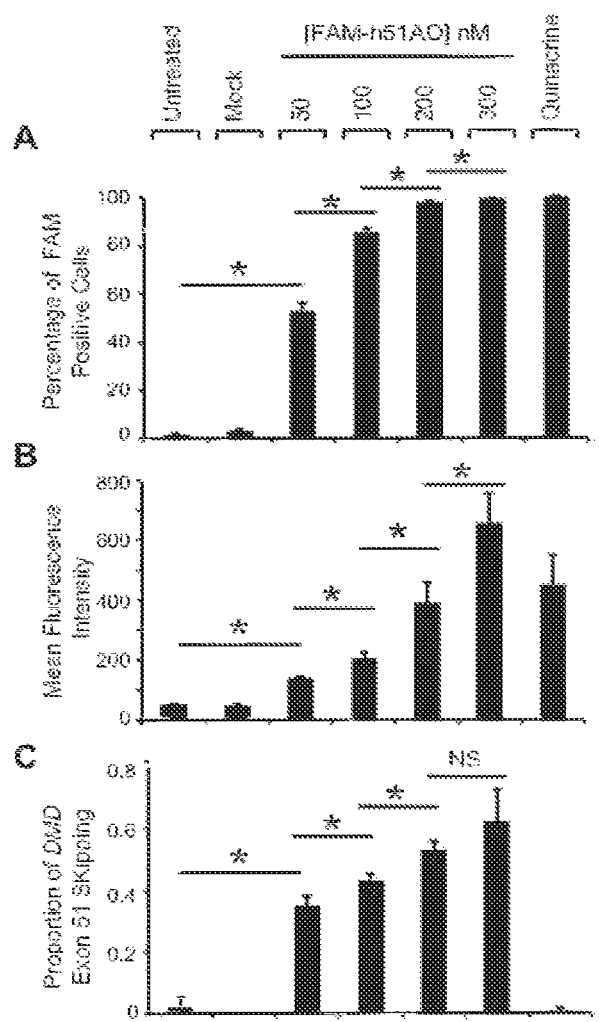
FIG. 1 shows the correlation of AO uptake and exon skipping activity in iDRM5017. On the seventh day of iDRM5017 fusion, 5' FAM labeled h51AON targeting DMD exon 51 was transfected for 24 hours after which it was removed. After 48 hours each well was harvested for analysis, and split in half. (A) After gating on live cells, the percentage of FAM (or AO) positive cells was determined. Quinacrine dihydrochloride, a nuclear dye that emits at the same wavelength as FAM, was used as a positive control. (B) Mean fluorescence intensity of populations described in A. (C) The other half of each well was analyzed for DMD exon 51 skipping activity. Total RNA was isolated a nested RT-PCR performed between DMD exons 43-52. This experiment was repeated twice, with each condition being represented in triplicate. Error bars represent s.d. * indicates P<0.05. P values were determined using a two tailed student's t-test.

The inventors present herein a combination of HTS data with a structure based clustering analysis in which 2-D descriptors and hierarchical clustering segregate biologically active from inactive compounds [34,35]. They report that compounds with similar 2-D structures possess comparable exon skipping activity in the screen [36]. Using a structure-activity relationship to guide their understanding of molecular targets and responsible signaling pathways for this observed exon skipping effect [37], they identify a number of active small molecules. An "active" small molecule, as used herein, refers to a small molecule which exhibits at least a measurable amount of modulation of splicing activity, such as enhancement of exon skipping, either in the presence of, or in the absence of, an AO which is specific for a splice sequence of interest (e.g. for an exon of interest to be skipped). Among these active small molecules are drugs which share several known molecular targets, including inhibition of calmodulin (CaM), an intracellular Ca2+-binding protein, highlighting the importance of calcium regulation in potentiating antisense based therapies [38,39].

Advantages of compounds and methods of the invention include that they augment the efficiency of exon skipping (e.g., when performed in the presence of AO) and thus allow a sufficient amount of skipping to be therapeutically relevant and/or reduce the cost resulting from high doses and repeated administration of expensive AOs.

One embodiment of the invention is a composition (combination) for enhancing exon skipping in a pre-mRNA of interest, comprising (a) a compound having a structural similarity to Flupentixol diHCl of 0.65 or greater, wherein the structural similarity is calculated using the algorithm in the ChemmineR package as described in Cao et al. (2008) *R. Bioinformatics* 24, 1733-1734, and wherein the compound is at least as effective as (about the same as or more effective than) Flupentixol diHCl in enhancing exon skipping in the pre-mRNA of interest when an effective amount of the compound is contacted with the pre-mRNA, provided that the compound is not Fluphenazine HCl, Trifluoperazine HCl or Piperacetazine, or a pharmaceutically acceptable salt, hydrate, solvate, or isomer of the compound, or (b) a compound having a structural similarity to Corynanthine HCl of 0.65 or greater, wherein the structural similarity is calculated using the algorithm in the ChemmineR package as described in Cao et al. (2008) *R. Bioinformatics* 24, 1733-1734, and wherein the compound is at least as effective as Corynanthine HCl in enhancing exon skipping in the pre-mRNA of interest when an effective amount of the compound is contacted with the pre-mRNA, provided that the compound is not Yohimbinic Acid M, Yohimbine HCl or Rauwolscine HCl, or a pharmaceutically acceptable salt, hydrate, solvate, or isomer of the compound, and, in combination with the compound of (a) or (b), (c) an antisense oligonucleotide (AO) that is specific for an exon that is to be skipped. Optionally, the composition may also comprise a pharmaceutically acceptable carrier.

The compounds of (a) and (b) above are sometimes referred to herein a "compounds of the invention." In embodiments of the invention, the compound of (a) above is Perphenazine, Flupentixol DiHCl or Zuclopenthixol, and/or the compound of (b) is Corynanthine HCl.

Cao et al. (2008) *R. Bioinformatics* 24, 1733-1734 is incorporated by reference herein, particularly with regard to its disclosure of methods for determining structural similarity of compounds. See the Examples herein for a further discussion of determination of such structural similarity.

Other embodiments of the invention include:

A method for enhancing exon skipping in a pre-mRNA of interest (e.g. from the muscle dystrophin (DMD) gene), comprising contacting the pre-mRNA with an effective amount of a compound of the invention, or a pharmaceutically acceptable salt, hydrate, solvate or isomer thereof. The compound may be administered in conjunction with the administration of an antisense oligonucleotide (AO) which is specific for a splicing sequence in the pre-mRNA, or it may be administered in the absence of such an AO. The method may be carried out in vitro or in a subject, such as, e.g., a subject that has Duchenne Muscular Dystrophy (DMD), is an animal model of DMD, or in another animal in which the exon skipping can be enhanced.

A method for treating a subject that has Duchenne Muscular Dystrophy (DMD), or is a non-human model of DMD, comprising administering to the subject an effective amount of a compound of the invention, or a pharmaceutically acceptable salt, hydrate, solvate, or isomer thereof, optionally in conjunction with an AO which is specific for a splicing sequence of exon 23, 45, 44, 50, 51, 52 and/or 53 of the DMD gene.

A method for identifying a compound (e.g. a small molecule) that enhances exon skipping in a pre-mRNA of interest, comprising testing candidate molecules for their ability to enhance exon skipping in the pre-mRNA, and selecting compounds which exhibit greater enhancement of exon skipping than, e.g., Perphenazine, Flupentixol DiHCl, Zuclopenthixol or Corynanthine HCl. In embodiments of the invention, the small molecule candidates are tested in conjunction with an AO specific for a splicing sequence of the exon to be skipped, or in the absence of such an AO. The small molecule candidate can be a variant of, e.g., Perphenazine, Flupentixol DiHCl, Zuclopenthixol or Corynanthine HCl.

A kit for carrying out one of the methods disclosed herein, comprising a compound (small molecule) of the invention or a pharmaceutically acceptable salt, hydrate, solvate, or isomer thereof and, optionally, an AO, wherein the compound and/or the AO are packaged in containers, separately or together.

A method for enhancing exon skipping in a pre-mRNA from the muscle dystrophin (DMD) gene, comprising contacting the pre-mRNA with a composition comprising (a) an agent that inhibits the Ryanodine Receptor (RyR1) (such as, e.g., dantrolene, Ryanodine or S107) and (b) an agent that inhibits calmodulin (CaM) (such as, e.g., Perphenazine, Flupentixol DiHCl, Zuclopenthixol or Corynanthine HCl) and, optionally, (c) an AO which is specific for a splicing sequence in the pre-mRNA.

The present inventors identify herein low molecular weight compounds (sometimes referred to herein interchangeably as "small molecules" or "small molecule compounds" or "compounds" of the invention) which block some forms of mRNA splicing and/or enhance (facilitate, augment, potentiate) other forms of mRNA splicing. A "small molecule" compound, as used herein, generally refers to a compound having a molecular weight less than about 540. The types of splicing that can be regulated by a method of the invention include alternative splicing, in particular exon skipping. Depending on factors such as the splicing sequence and the gene or exon involved, this modulation of splicing can be accomplished in the presence of, or in the absence of antisense oligonucleotides (AOs) that are specific for splicing sequences of interest. In embodiments of the invention, a compound (small molecule) and an AO of the invention act synergistically. The compounds of the invention act on a precursor mRNA (pre-mRNA) of interest, which is then spliced to form a mature mRNA. The antisense molecules used in a method of the invention are sometimes referred to herein as antisense "splice switching oligonucleotides (SSO's)."

It is to be understood that references herein to a compound of the invention include pharmaceutically acceptable salts, hydrates, solvates or isomers thereof. For example, sodium ions in the formulas can be substituted with any of a variety of other pharmaceutically acceptable cations. Suitable such salts, hydrates, solvates or isomers will be evident to a skilled worker. See, e.g., Remington's Pharmaceutical Sciences, 18$^{th}$ edition (1990, Mack Publishing Co., Easton, Pa.).

As shown in the Examples herein, the inventors, starting with over 5120 small molecule compounds, identified several classes (clusters) of small molecules, each of which shares a common 2-D structure. Further assays, in vitro or in animal models, in the presence or absence of AOs, led to the identification of a number of small molecule compounds which enhance exon skipping for a variety of DMD exons, either alone or in synergy with an AO. Among the active small molecules identified herein are Perphenazine, Flupentixol DiHCl, Zuclopenthixol and Corynanthine HCl. The active small molecule compounds identified herein are sometimes referred to as small molecule compounds or small molecules or compounds "of the invention." This includes the four compounds noted above as well as the classes of molecules defined by virtue of similar 2-D structures and activity levels, as described herein. It is expected that at least some of the compounds of the invention will induce (enhance) exon skipping and create alternate splice forms of proteins that are relevant to a variety of disease states.

The active compounds of the invention have different known effects on cells and have been used for different therapeutic purposes. How each of the compounds affects the RNA splicing machinery to alter the efficiency of exclusion of targeted exons is not known at this time. While the detailed molecular mechanisms are not yet established, several of the compounds identified have well-characterized effects in cells and in humans. However, none of the identified compounds has been used in order to alter exon splicing therapeutically, and none of them has been used to treat the class of patients who would benefit from a modulation of exon splicing, such as exon skipping.

It is expected that endogenously generated antisense oligonucleotides (for instance from gene delivery) will augment exon skipping in a similar manner as exogenously administered AOs. For example, endogenously generated small nuclear RNA (sRNA) carrying appropriate antisense sequences and transcribed from, e.g., a U7 snRNA-based gene construct can be used in a method of the invention.

"Antisense-mediated exon skipping," as used herein, refers to an approach that uses antisense oligonucleotides (AOs) to modulate splicing by blocking (hiding) specific sequence motifs in the pre-mRNA (sometimes referred to herein as "splicing sequences") essential for exon inclusion from the splicing machinery. AOs that block aberrant splice sites can restore normal splicing. Alternatively, AOs targeting certain splicing sequences can switch splicing patterns from detrimental to beneficial isoforms or can convert at least partially non-functional mRNAs into functional mRNA. An example of the latter approach is the restoration of a disrupted reading frame, thereby generating a semi-functional protein instead of a non-functional proteins.

A compound of the invention can be used to block splicing at a site of interest by specifically interacting with (e.g., binding to) a splicing sequence at that site, either directly or indirectly. By a "splicing sequence" is meant a sequence that regulates and/or is required for splicing out of a particular intron and/or the retention of a particular exon. The splicing sequence can be, for example, a splice donor site, a splice acceptor site, a branch site, an intronic splicing enhancer (ISE), an exonic splicing enhancer (ESE), an intronic splicing silencer or an exonic splicing silencer.

An AO used in a method of the invention can bind directly and specifically to a target splicing sequence of interest. By "specific binding" is meant that the AO binds preferentially to the target sequence of interest, but not to non-target sequences under conditions in which specific binding is desired. The conditions can be, e.g., physiological conditions in the case of in vivo assays or therapeutic treatment, and for in vitro assays, conditions in which the assays are performed. Because the mechanism by which small molecule compounds of the invention block splicing (e.g., enhance exon skipping) is not known for all of the compounds, it is not known whether the compound binds directly to a splice site or acts indirectly (e.g., by binding to another RNA or protein element of a spliceosome). Regardless of the mechanism, a compound of the invention that "specifically" blocks a splicing event of interest is one that preferentially blocks the particular splicing event but does not block non-targeted splicing events, under conditions in which specific blocking is desired.

As used herein, the term "antisense oligonucleotide (AO)" refers to a single-stranded oligonucleotide that is specific for, and complementary to, a splicing sequence of interest, and accordingly is capable of hydrogen bonding to the sequence. One of skill in the art can readily design AOs to be specific for suitable target sequences, many of which are well-known in the art. For example, one can access pre-mRNA sequences comprising suitable splicing sequences in publications or in annotated, publically available databases, such as the GenBank database operated by the NCBI. A skilled worker will be able to design, make and use suitable antisense oligonucleotides, based on these or other sequences, without undue experimentation. A number of AO's have been designed for enhancing exon skipping and some are currently in preclinical or clinical trials. Any of these AOs is suitable for use in a method of the invention.

An antisense nucleic acid may be, e.g., an oligonucleotide, or a nucleic acid comprising an antisense sequence that is operably linked to an expression control sequence and that is expressed in a cell.

Antisense oligonucleotides may have a variety of different backbone chemistries, such as morpholino phosphorodiamidate (PMO) or 2'-O-methyl' or peptide nucleic acids, etc., which stabilize them. For example, an antisense oligonucleotide can be DNA, RNA, PNA or LNA, or chimeric mixtures or derivatives or modified versions thereof. The nucleic acid can be modified at the base moiety, sugar moiety, or phosphate backbone, using conventional procedures and modifications. Modifications of the bases include, e.g., methylated versions of purines or pyrimidines. Modifications may include other appending groups that will be evident to a skilled worker.

Antisense oligonucleotides can be constructed using chemical synthesis procedures known in the art. An AO can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. For guidance in methods of synthesizing AOs used in methods of the present invention, see, e.g. the following:

For guidance in methods of synthesizing morpholino AO's for use in the present invention, see, e.g., US patent application 2009/0131624 ("Synthesis of morpholino oligomers using double protected guanine morpholino subunits").

For guidance in synthesizing oligonucleotides, see, e.g., Gough et al. (1979) *Nucleic Acids Research* 7, 1955-1964; Hata et al. (1983) *Tetrahedron Lett.* 24, 2775-2778; Jones et al. (1982A *Tetrahedron Lett.* 23, 2253-2256; Jones et al. (1982) *Tetrahedron Lett.* 23, 2257-2260; O. Mitsunobu (1981) *Synthesis* 1, 1-28; Reese et al. (1981) *Tetrahedron Lett.* 22, 4755-4758; Reese et al. (1984) *J. Chem. Soc., Perkin Trans.* 11263-1270; Summerton et al. (1993) U.S. Pat. No. 5,185,444; Summerton et al. (1997) *Antisense Nucl. Acid Drug Dev.* 7(3), 187-195.

For guidance in synthesizing 2-O-methyl' oligos, see e.g. Verma et al. (1998) MODIFIED OLIGONUCLEOTIDES: Synthesis and Strategy for Users, *Annu. Rev. Biochem.* 67, 99-134

Small molecules of the invention can be synthesized using conventional methods. Many of the compounds discussed herein are commercially available.

To enhance exon skipping in cells in culture, AO's can be added to cells in culture media. Typically, synthetic oligonucleotides are added to a final concentration of about 10 nM to about 10 microM, e.g., about 50 nM to about 1000 nM (e.g., at increments of 10 nM within the indicated ranges). The term "about" a particular value, as used herein, means plus or minus 10% of the indicated value.

Effective doses of AOs for in vivo administration can be determined, e.g., on the basis of the amounts used for exon skipping in the absence of a small molecule of the present invention. Many AO's have been administered to subjects in the absence of small molecule compounds of the invention, and doses have been established which are at least partially effective and are non-toxic to the subjects. In general, doses of AOs ranging from about 5-100 mg/kg/wk IV (intravenous) (or comparable amounts for other modes of administration) are effective for inducing at least a detectable amount of dystrophin expression with targeted removal of a given exon.

Alternatively, an antisense oligonucleotide can be produced biologically using an expression vector into which a nucleic acid has been subcloned in an antisense orientation (i.e., nucleic acid transcribed from the inserted nucleic acid will be of an antisense orientation to a target sequence of interest). Expression control sequences (e.g., regulatory sequences) operatively linked to a nucleic acid cloned in the antisense orientation can be chosen which direct the expression of the antisense RNA molecule in a cell of interest. For instance, promoters and/or enhancers or other regulatory sequences can be chosen which direct constitutive, tissue specific or inducible expression of an AO. Inducible expression of antisense RNA, regulated by an inducible eukaryotic regulatory system, such as the Tet system (e.g., as described in Gossen et al. (1992) *Proc. Natl. Acad. Sci. USA* 89, 5547-5551; Gossen et al. (1995) *Science* 268, 1766-1769; PCT Publication No. WO 94/29442; and PCT Publication No. WO 96/01313) can be used. The antisense expression vector can be in the form of, for example, a recombinant plasmid, phagemid or attenuated virus. Suitable viral vectors include, e.g., adeno-associated virus (AAV) or lentivirus vectors. The antisense expression vector can be introduced into cells using standard techniques well known in the art. For guidance in using AAV vectors for introducing antisense molecules into mdx mice, see e.g. Denti et al. (2008) *Hum Gene Ther.* 19, 601-608 or Incitti et al. (2010) *Mol. Ther.* 18, 1675-1682.

In one embodiment of the invention, an RNA molecule that comprises the sequence antisense to a splicing sequence in, e.g., the dystrophin pre-mRNA, is produced biologically by using an expression vector into which a nucleic acid has been subcloned. Expression control sequences (e.g. regulatory sequences) operably linked to the cloned nucleic acid can be chosen which direct the expression of the antisense RNA molecule comprising the sequence antisense to a splicing sequence in, e.g., dystrophin pre-mRNA, in a cell of interest. The RNA molecule may comprise, e.g., a U1 snRNA, U2 snRNA, U6 snRNA or U7 snRNA. Without wishing to be limited by any particular mechanism, it is suggested that expression of the snRNA generates an snRNP particle which then binds to the target sequence in dystrophin pre-mRNA via the complementary fragment of snRNA. Any of the types of expression control sequences described in the previous paragraph can be used to direct the expression of the desired RNA in this embodiment.

In one embodiment of the invention, an AO comprises a strand that is completely complementary (100% identical in sequence) to a splicing sequence that it is designed to inhibit. That is, every contiguous nucleotide in the AO is hybridized to every nucleotide in a splicing sequence. However, 100% sequence identity between the AO and the target splicing sequence is not required to practice the present invention. Thus, the invention has the advantage of being able to tolerate naturally occurring sequence variations that might be expected due to genetic mutation, strain polymorphism, or evolutionary divergence. Alternatively, the variants may be artificially generated. Nucleic acid sequences with, e.g., small insertions, deletions, and single point mutations relative to the target sequence can be effective for inhibition. The degree of sequence identity can be, e.g., 95%, 98%, 99%, or 100%. Such a variant AO must, of course, retain the relevant activity of the AO from which it is derived. (e.g., the ability to suppress splicing at a site of interest). Such variants are sometimes referred to herein as "active variants."

The length of an AO may vary, provided that it is capable of binding selectively to the intended splicing sequence within the pre-mRNA molecule. A skilled worker can readily determine a satisfactory length. Generally, an AO is from about 10 nt in length to about 50 nt in length. Any length of nucleotides within this range, including the endpoints, can be used in a method of the invention. In one embodiment, the length of the AO is about 17-30 nt in length.

For further guidance for designing suitable antisense molecules that are complementary to a region of a pre-mRNA involved in splicing (thereby blocking splicing), and for methods for making and delivering such molecules to a cell or a subject, see, e.g., US 2008/0200409 or U.S. Pat. Nos. 7,973,015, 7,960,541, 7,902,160, 7,888,012, 7,879,992 or 7,737,110.

A method of the invention can be carried out in vitro (e.g., to elucidate the mechanism by which splicing occurs, such as to reveal novel molecular interactions in the processing of mRNA; or to screen for compounds that can block a splicing event and thus, for example, enhance exon skipping).

In another embodiment of the invention, the method is carried out in a subject, in vivo. A "subject," as used herein, can refer to any animal which is subject to a disease or condition that can be treated by a method of the invention. Suitable subjects include, e.g., a mammal, such as an experimental animal or disease model, a farm animal, pet, or the like. In some embodiments, the animal is a primate, for example a human.

In some embodiments of the invention, a subject is treated with an effective amount of a compound of the invention, or with a composition of a compound of the invention and a suitable AO, each of which is designed to block a splicing event of interest. An "effective amount" of a compound (or composition) of the invention is an amount that is effective to elicit a measurable amount of biological activity, e.g. a measurable amount of enhancement of exon skipping (in some embodiments in the absence of AOs, and in some embodiments in the presence of a suitable AO). Preferably, an effective amount of a compound or composition of the invention does not elicit substantial amounts of undesirable (e.g., toxic) effects. The enhancement can occur prophylactically (e.g. preventively, to inhibit the development of the disorder), or in a subject who already has the condition. For example, treatment by a method of the invention can ameliorate one or more symptoms of the condition.

In some embodiments, one or more of the compounds of the invention is administered in conjunction with one or more active small molecules identified herein and/or with one or more of the active small molecules which are disclosed and characterized in the PCT application published as WO2013/033407, which is incorporated by reference in its entirety herein. These small molecules include, e.g., furaltadone hydrochloride, 5-iodotubericidin, bendroflumethiazide, cyclopiazonic acid, GW 5074, indirubin, rescinnamin, U-0126, acetopromazine maleate salt, Ro 31-8220, dantrolene, Revonto (which is an alternative formulation of dantrolene), dichlorobenzamil, ellipticine, fenbendazole, GF 109203X, halofantrine, niclosamide, pimozide, reserpine, syringospine, Ryanodine, RyCal S107, piperacetazine, fluphenazine dihydrochloride, trifluorperazine dihydrochloride, yohimbinic acid, and menadione.

A skilled worker will recognize a variety of conditions that can be treated by a method of the invention. A probabilistic analysis indicated that over 60% of human disease-causing mutations affect splicing rather than directly affecting coding sequences (Lopez-Bigas et al. (2005) *FEBS Letters* 579, 1900-3). See also Wang et al. (2007), Splicing in disease: disruption of the splicing code and the decoding machinery, *Nature Reviews Genetics* 8, 749-761 and Singh et al. (2012), Pre-mRNA splicing in disease and therapeutics, *Trends in Molecular Medicine* 18, (8), 472-482. Diseases associated with aberrant splicing or missplicing that can be inhibited by a method of the invention include e.g. beta-thalassemia and certain forms of cancers. Alternatively, exon skipping by a method of the invention can remove exons that contain mutations which are associated with diseases, such as mutations that alter the reading frame of the protein encoded by an mRNA. These conditions include, e.g., DMD, as described above (changing DMD dystrophin to a more functional form of dystrophin, in effect converting Duchenne MD into Becker MD). One embodiment of the invention is a method for treating a subject that has Duchenne muscular dystrophy (DMD), or is a non-human model of DMD, comprising administering to the subject an effective amount of small molecule selected from the compounds of the invention, in conjunction with an AO specific for modulating splicing of dystrophin pre-mRNA, such as one for exon 23, 44, 45, 50, 51, 52, or 53 of the DMD gene. The exon skipping can be either single or multi-exon skipping (e.g., skipping of many possible 2-10 exon combinations that will be evident to a skilled worker).

Suitable exons that can be skipped by a method of the invention will be evident to a skilled worker. See, e.g., Table 6 in WO2013/033407, which lists human DMD coding sequences with 50 intronic nucleotides at the exon boundaries and indicates mRNA sequences and intronic sequences. On the basis of such sequences, a skilled worker can readily design AO's specific for blocking the relevant splice sites.

Exons for which exon skipping can be therapeutic, for the treatment of muscular dystrophy and other conditions, will be evident to a skilled worker. There is a substantial literature on the design of specific exons in DMD and many thousands of other exons in the human genome potentially amenable to exon skipping. For instance, a nonsense mutation within an exon which if deleted would not alter the reading frame, may be able to be removed from the mature RNA by targeted removal by exon skipping. The possible exons in the human genome are too numerous to list. In the DMD gene alone, there are 79 exons and many sequences that can be used to partially block inclusion of a given exon (from exon 2-exon 78) that are therapeutically relevant. For example, in 2007, Wilton et al described a series of oligos that can skip single exons across the DMD gene. (Wilton et al (2007) *Mol Ther.* 15, 1288-1296). Other work by Pramono et al demonstrates oligo design principles (Pramono et al. (2012) *Hum Gene Ther* 23(7), 781-90). Malueka et al describe a decision metric for oligo targeting in DMD (Malueka et al (2012) *BMC Genet.* 13, 23). Popplewell, et al also describe design principles for the oligo component of the combined therapeutic described in the present invention (Popplewell, et al (2012) *Methods Mol Biol.* 867, 143-67). Further, recently published work by Aoki, et al describe the skipping of multiple exons from exon 45-55 in mouse (Aoki, et al (2012) *Proc Natl Acad Sci USA.* 109 (34), 13763-8). This is therapeutically relevant for human Duchenne therapy as well as up to 65% of all DMD affected individuals could be treated by this cocktail. Since the described invention works on multiple independent exons, it is expected that the chemical entities described herein will improve the removal of specific individual and sets of exons from the mature transcript in vivo and in vitro. The general field of AO design for DMD is described in Aarstma-Rus, 2012 and Lu, 2011. Further, the removal of exonic duplications (see Aartsma-Rus (2007), *BMC Med Genet.* 5, 8:43) commonly observed in DMD may also be improved by combination use with the compounds described herein.

For reviews of conditions or diseases that can be treated by a method of the invention, see, e.g., Bauman et al. (2011) *Bioeng. Bugs.* 2, 125-8, Hammond et al. (2011) *Trends Genet.* 27, 196-205, Wood et al. (2010) *Brain* 133, 957-72 or Sazani et al., "Splice-switching oligonucleotides as potential therapeutics" (2007) in Antisense Drug Technology: Principles, Strategies, and Applications, Second Edition (Ed. S. T. Crooke) 89-114 (CRC Press, Boca Raton). Among the diseases treatable by modulation of exon skipping are, e.g., spinal muscle atrophy (SMA), Hutchinson-Gilford progeria syndrome (HGPS), beta-thalassemia, Ataxia telangiectasia (ATM), dysferlinopathies, frontotemporal dementia and cystic fibrosis.

In embodiments of the invention, a compound of the invention is administered to a subject, e.g. as part of an adjuvant treatment, or is contacted (e.g., in vitro) with a pre-mRNA target of interest, in conjunction with a suitable AO that is designed to specifically block a splicing event of interest. "In conjunction with" means that the AO can be administered before, or at the same time as, or after, the compound, and that the two components can be administered in separate delivery vehicles or in the same delivery vehicle. The two agents can be administered with the same, or different, dosage regimens. As used herein, the singular forms "a," "an," and "the" include plural referents unless the context clearly dictates otherwise. For example, "a" compound of the invention as used above means one or more compounds, which can be the same or different; and "an" AO as used above means one or more AO molecules, which can be the same or different.

A number of considerations are generally taken into account in designing delivery systems, routes of administration, and formulations for compounds or compositions of compounds and an AO of the invention. The appropriate delivery system for an agent of the invention will depend upon its particular nature, the particular clinical application, and the site of drug action. One skilled in the art can easily determine the appropriate dose, schedule, and method of administration for the exact formulation of the composition being used, in order to achieve the desired response in the individual patient.

Any of a variety of conventional methods can be used to introduce AOs and/or small molecules of the invention into cells, in vitro or in vivo. These methods include, for example, transfection, electroporation, hydrodynamic "high pressure" delivery, nanoparticle delivery, liposomes, colloidal dispersal systems, or other methods known in the art.

Intracellular AO delivery can be enhanced by conjugating cell penetrating peptides to the AO using methods and compounds known in the art. See, e.g., U.S. Pat. No. 7,468,418 and PCT publications WO2009/005793 and WO2009/147368.

Compounds and AO's can be administered (delivered) to a subject by the same or by different modes of administration. Suitable modes of administration include, e.g., subcutaneous, intramuscular, intravenous, oral, intranasal, cutaneous, or suppository routes, depending on the formulation, the compound, and the condition to be treated. Compounds and AO's of the invention may be delivered via a variety of routes including all of the above routes, in dosing patterns that can be optimized with routine, conventional methods. In one embodiment, the compounds are administered chronically to subjects (patients) in conjunction with therapeutic antisense oligonucleotides. In some embodiments, a compound of the invention is administered frequently (e.g., daily or more frequently) to augment less frequent (e.g., monthly or weekly) administration, such as by intravenous or subcutaneous injection, of AO.

Formulations for delivery by a particular method (e.g., solutions, buffers, and preservatives) can be optimized by routine, conventional methods that are well-known in the art. See, e.g., Remington's Pharmaceutical Sciences, 18$^{th}$ edition (1990, Mack Publishing Co., Easton, Pa.). for guidance in suitable formulations.

An "effective" dose of an agent of the invention (either a compound, or a compound in conjunction with an AO, or the AO), or composition thereof, is a dose that, when administered to an animal, particularly a human, in the context of the present invention, is sufficient to effect at least a detectable amount of a therapeutic response in the individual over a reasonable time frame.

The exact amount of the dose (of a small molecule of the invention, used alone or in conjunction with an AO, or of the AO), will vary from subject to subject, depending on the species, age, weight and general condition of the subject, the severity or mechanism of any disorder being treated, the particular agent or vehicle used, its mode of administration and the like. The dose will also be a function of the exon that is being skipped/removed from the mature RNA and the sequence of the AO. The dose used to achieve a desired effect in vivo will be determined by the potency of the particular agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

For example, a dose of a small molecule of the invention can range from about 4-10 mg/kg/day, or can be higher or lower. In general, the dose of a small molecule of the invention is one, or close to one, which has been shown to be safe for subjects, such as human patients. Dantrolene, for example, has been shown to be safe when administered to humans up to 8 mg/kg/day during long term administration. Suitable oral doses of Dantrolene include doses of about 4-10, e.g. about 6-8, mg/kg/day. A functional benefit (wire hang test in mdx mice) was shown in WO2013/033407, using 10 mg/kg/week of the oligo AON23 and dantrolene at 10 mg/kg/day compared to 10 mg/kg/week of the AON23 alone (p=0.022).

Dosages for administration of a therapeutic agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other therapeutic agents, calculated in an amount sufficient to produce the desired effect in association with a pharmaceutically acceptable diluent, carrier, or vehicle.

One embodiment of the invention is a method for identifying a small molecule compound that enhances exon skipping in an mRNA of interest, comprising testing candidate small molecules, such as variants of a compound of the present invention, for their ability to enhance exon skipping in the mRNA, and selecting compounds which exhibit the same or greater enhancement activity than the starting (non-variant) compound. The screening method can be carried out in the absence of, or in conjunction with, an AO specific for a splicing sequence of the exon that is to be skipped. In some embodiments, the variants are FDA-approved drugs.

In one embodiment, the method comprises contacting a suitable cell (in vitro or in vivo) with a putative small molecule compound, such as a variant of one of the compounds of the invention, and measuring the amount of splicing or, in one embodiment, of exon skipping, of interest. Any of the assays discussed herein can be adapted to such a screen. The amount of splicing or exon skipping can be compared to a control value. For example, for an assay which is conducted in the absence of an AO, the control can be a cell that has not been contacted with the compound. For an assay which is conducted in the presence of a suitable AO, the control can be a cell that is contacted with the AO but not the putative compound. A statistically significant decrease in the amount of splicing or increase in the amount of exon skipping in the test cells compared to the control is indicative that the putative compound is superior to the compound from which it has been derived, or to a suitable arbitrarily selected control compound.

Suitable variant compounds that can be tested will be evident to a skilled worker. For example, a substituent on, e.g., an aromatic or non-aromatic carbon can be substituted with H, alkyl, alkoxy, hydroxyalkyl, thioalkyl, haloalkyl, aminoalkyl, alkoxyalkyl, alkylaminoalkyl, etc. Some suitable variants are discussed below. Others will be evident to a skilled worker. Suitable (e.g., improved) variant compounds that are identified by such a screen are also included in the invention, and are sometimes referred to herein as "active variants" of the compounds. An "active variant," as used herein, refers to a compound which retains at least one activity of the compound of which it is a variant, e.g. the ability to block splicing of an exon of interest.

The terms "alkyl" used alone or as part of a larger moiety (i.e. "alkoxy," "hydroxyalkyl," "alkoxyalkyl," and "alkoxycarbonyl") include both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkoxy" refers to an —O-alkyl radical, such as, for example —O-Me, —O-Et, —O—Pr, and so on. The term "hydroxyalkyl" refers to an alkyl group substituted with one or more hydroxyl, such as, for example, hydroxymethyl, 1-hydroxyethyl, 2-hydroxyethyl, 1,2-dihydroxyethyl, and so forth. The term "thioalkyl" refers to an —S-alkyl group, such as, for example, example —S-Me, —S-Et, —S—Pr. The term "haloalkyl" means alkyl, substituted with one or more halogen atoms, such as trifluoromethyl, chloromethyl, 2,2,2-trifluoroethyl, 1,1,2,2, 2,-petanfluoroethyl, and so on. The term "aminoalkyl" means alkyl, substituted with an amine group ($NH_2$), such as, for example, aminomethyl, 1-aminoethyl, 2-aminoethyl, 3-aminopropyl and so forth. The term "alkoxyalkyl" refers to an alkyl group, substituted with an alkoxy group, such as, for example, methoxymethyl, ethoxymethyl, methoxyethyl, and so forth. As used herein, the term "alkylaminoalkyl" refers to an alkyl group substituted with an alkylamine group, such as, for example, N-methylaminomethyl, N,N-dimethylaminomethyl, N,N-methylpentylaminomethyl, 2-(N-methylamino)ethyl, 2-(N,N-dimethylamino)ethyl, and so forth.

The term "halogen" or "halo" means F, Cl, Br, or I.

The term "nitro" means (—$NO_2$).

The term "amine" or "amino" used alone or as part of a larger moiety refers to unsubstituted (—$NH_2$). The term "alkylamine" refers to mono- (—NRH) or di-substituted (—$NR_2$) amine where at least one R group is an alkyl substituent, as defined above. Examples include methylamino (—$NHCH_3$), dimethylamino (—$N(CH_3)_2$). The term "arylamine" refers to a mono (—NRH) or di-substituted (—$NR_2$) amine, where at least one R group is an aryl group as defined below, including, for example, phenylamino, diphenylamino, and so forth. The term "heteroarylamine" refers to a mono (—NRH) or di-substituted (—$NR_2$) amine, where at least one R group is a heteroaryl group as defined below, including, for example, 2-pyridylamino, 3-pyridylamino and so forth. The term "aralkylamine" refers to a mono (—NRH) or di-substituted (—$NR_2$) amine, where at least one R group is an aralkyl group, including, for example, benzylamino, phenethylamino, and so forth. The term "heteroaralkylamine" refers to a mono (—NRH) or di-substituted (—$NR_2$) amine, where at least one R group is a heteroaralkyl group. As used herein, the term "alkylaminoalkyl" refers to an alkyl group substituted with an alkylamine group. Analogously, "arylaminoalkyl" refers to an alkyl group substituted with an arylamine, and so forth, for any substituted amine described herein.

The term "alkenyl" used alone or as part of a larger moiety include both straight and branched chains containing at least one double bond and two to ten carbon atoms (i.e. 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "aryl" used alone or as part of a larger moiety, refers to mono-, bi-, or tricyclic aromatic hydrocarbon ring systems having five to fourteen members, such as phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. The term "aralkyl" refers to an alkyl substituent substituted by an aryl group. The term "aryloxy" refers to an —O-aryl group, such as, for example phenoxy, 4-chlorophenoxy and so forth. The term "arylthio" refers to an —S-aryl group such as, for example phenylthio, 4-chlorophenylthio, and so forth. The term "aryl" used alone or as part of a larger moiety also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, and alkylthio, O-acyl, N-acyl, S-acyl as defined herein.

The term "heteroaryl", used alone or as part of a larger moiety, refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic." The term "heteroaralkyl" refers to an alkyl group substituted by a heteroaryl, such as, for example, 2-pyridylmethyl, 3-pyridylmethyl, 1-imidazolomethyl, 2-imidazolomethyl and so forth. The term "heteroaryloxy" refers to an —O-heteroaryl group. The term "heteroarylthio" refers to an —S-aryl group. A heteroaryl group may have more than one substituent, up to the total number of free substitution positions. For example, a heteroaryl group may have 1, 2, 3, 4, or 5 substituents. The substituents may the same or different. Substituents on a heteroaryl group include hydrogen, halogen, alkyl, alkenyl, nitro, hydroxyl, amino, alkylamino, alkoxy, and alkylthio, O-acyl, N-acyl, S-acyl as defined herein.

The term "O-acyl" refers to an "—O—C(O)-alkyl," "—O—C(O)-aryl," or "—O—C(O)— heteroaryl" group. The term "N-acyl" refers to an "—NR—C(O)-alkyl," "—NR—C(O)-aryl," or "—NR—C(O)-heteroaryl" where R is an alkyl, hydroxyl, or alkoxy group. The term "S-acyl"

refers to "—S—C(O)-alkyl," "—S—C(O)-aryl," or "—S—C(O)-heteroaryl." The term "N—O-acyl" refers to an "N—O—C(O)-alkyl," "N—O—C(O)-aryl," or "N—O—C(O)-heteroaryl" group.

As used herein, a "substituted" structure refers to a chemical structure where a hydrogen atom has been replaced by a substituent. A "substituent" is a chemical structure that replaces a hydrogen atom on the substituted structure. The term "substituent" does not imply that the substituent is smaller than the substituted structure.

Another embodiment of the invention is a composition for enhancing exon skipping in an mRNA of interest, comprising a compound of the invention and an AO that is specific for an exon that is to be skipped, and, optionally, a pharmaceutically acceptable carrier. In one embodiment, the composition comprises a dosage form of a compound of the invention and a dosage form of an AO that is specific for the exon which is to be skipped.

Suitable pharmaceutically acceptable carriers will be evident to a skilled worker. For guidance, see, e.g., Remington's Pharmaceutical Sciences (supra).

Another embodiment of the invention is a kit for carrying out one of the methods of the invention. For example, a kit for enhancing exon skipping in a pre-mRNA of interest can comprise a compound of the invention and an AO that is specific for an exon splicing sequence in the mRNA of interest. A kit for enhancing exon skipping in a muscle dystrophin mRNA in a subject that has Duchenne Muscular Dystrophy (DMD), in an animal model of DMD, or in an animal that is not necessarily an animal model for DMD, such as a monkey, can comprise a dosage form of a compound of the invention and a dosage form of an AO that is specific for the exon which is to be skipped.

A kit of the invention can comprise a device, composition, or other means for administering the agents of the invention to a subject. A kit suitable for a therapeutic treatment in a subject may further comprise a pharmaceutically acceptable carrier and, optionally, a container or packaging material.

Optionally, the kits comprise instructions for performing the method, and/or a notice in the form prescribed by a governmental agency regulating the manufacture, use or sale of pharmaceuticals or biological products (such as the FDA), which notice reflects approval by the agency of manufacture, use or sale for human administration. In addition, agents in a kit of the invention may comprise other therapeutic compounds, for combination therapy. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form for use as therapeutics, or in single reaction form for diagnostic use.

Methods for making and using antisense and/or small molecule reagents, and for testing them for desirable properties, are conventional and well-known in the art. Guidance in performing some of the methods of the invention is provided, for example, in Sambrook et al., Molecular Cloning, A Laboratory Manual (volumes Cold Spring Harbor Laboratory Press, USA or Harlowe and Lane, Antibodies a Laboratory Manual 1988 and 1998, Cold Spring Harbor Laboratory Press, USA. These and other references cited herein which provide guidance for performing methods related to the present invention are incorporated by reference herein in their entirety.

In the foregoing and in the following examples, all temperatures are set forth in uncorrected degrees Celsius; and, unless otherwise indicated, all parts and percentages are by weight.

EXAMPLES

Example I. Materials and Methods

High-Throughput Screen in the Ex50GFP Reporter Cell Line

A stable clone was generated from C2C12 cells transfected with a human exon-50 DMD GFP reporter (ex50GFP) [32]. Ex50GFP myoblasts were seeded at a density of 4,000 cells per well into uncoated 384 well plates in myoblast growth media (Phenol red free DMEM, 15% FBS, 1× L-glutamine and 1× Pen/Strep). Cells were incubated for 4 hours either with or without (n=2 replicates), 300 nM of 2'-O-methyl phosphorothioate h50AON (−19+8) 5'-AAC-UUCCUCUUUAACAGAAAAGCAUAC-3'] (SEQ ID NO:1) targeting exon 50 skipping by masking the intron-exon boundary at the 3' intron 49 splice acceptor site. h50AON was transfected using FUGENE (Roche) at a ratio of 3 µL FUGENE:1 µg DNA. Following h50AON incubation, the Prestwick library (n=1120, across 4 plates) was screened in duplicate at a 10 µM concentration with a final concentration of 1% DMSO carrier. The final well volume was 50 µL. Forty-eight hours later DNA was stained with Hoescht (Sigma) by adding 100 µg/mL final concentration and incubating for 30 min at 37° C. Following Hoescht incubation, fluorescence was measured using MicroXpress with GFP fluorescence having an exposure setting of 350 ms and Hoescht at 21 ms.

High-Throughput Screen Normalization and Analysis

Analysis of high-throughput screening data was performed using a custom script in MatLab (R2011a). Each screen was normalized in a step-wise fashion first on an intra-plate basis, and then across plates (n=4 plates). Rows (n=22 elements per row) were normalized by dividing the fluorescence for each well ($\Psi$well) by the mean of the entire row ($\mu\Psi$row), and then multiplying by the mean plate fluorescence ($\mu\Psi$plate) (shown in equation 1). Columns (n=14 elements) were then normalized using the same strategy (shown in equation 2).

$$\varphi\_norm = \varphi\_well / [\![\mu\varphi]\!]\_row \times [\![\mu\varphi]\!]\_plate \qquad (1)$$

$$\varphi\_norm = \varphi\_well / [\![\mu\varphi]\!]\_column \times [\![\mu\varphi]\!]\_plate \qquad (2)$$

Interplate normalization was performed as follows. Row fluorescence ($\Psi$row) was divided by the row means of all four plates ($\mu\Psi$rows), and multiplied by the mean fluorescence from all plates ($\mu\Psi$plates) (shown in equation 3). Columns were then normalized using the same strategy (shown in equation 4). Duplicate plates from independent screening days were then averaged and normalized.

$$\varphi\_norm = \varphi\_row / [\![\mu\varphi]\!]\_rows \times [\![\mu\varphi]\!]\_plates \qquad (3)$$

$$[\![\varphi]\!]\_norm = \varphi\_column / [\![\mu\varphi]\!]\_columns \times [\![\mu\varphi]\!]\_plates \qquad (4)$$

To determine compound performance in the screens the Z score was calculated by comparing the normalized fluorescence of each compound to that of the DMSO controls on all plates (n=128). The Z score was calculated for the 'Compound only' and 'Compound+AO' screen using equation 5.

$$Z = [\![(\varphi [\![\_(compound) - [\![\mu\varphi]\!]\_dmso)/\sigma\_dmso \qquad (5)$$

For the ratio analysis additional steps were taken so that the 'Compound+AO' screen and 'Compound only' screen could be directly compared. To find the overall effect of adding AO on fluorescence readouts, the mean fluorescence values from the DMSO controls for the Compound+AO' screen were divided by the DMSO controls in the 'Compound only' screen. This number was 2.52. Therefore, all 'Compound+AO' normalized fluorescence values were divided by 2.52, followed by the division of the corresponding 'Compound only' fluorescence values. The ratio Z score was then calculated using equation 5. Hierarchical clustering analysis on screen performance was performed in Matlab.

2-D Structural Clustering

A 2-D structure-based clustering algorithm was applied to the Prestwick libraries to determine if common structural motifs were responsible for exon skipping activity using the ChemmineR package in R (Version 3.0.1) [40]. Compound library SDF files were clustered into discrete similarity groups with the binning clustering function that determines compound similarity utilizing multiple user-defined cutoffs. SDF files were also obtained for 4009 ligands with crystal structures bound to their respective protein targets from the Research Collaboratory for Structural Bioinformatics Protein Data Bank (PDB). In both cases, after a heuristic search in which the libraries were clustered with a range of cut-offs the optimal threshold for similarity cutoff was determined to be 0.65, which is near suggested values that have been previously published [40,41].

Compounds

The following compounds were obtained from Sigma-Aldrich: Quinacrine dihydrochloride (CAS#6151-30-0), Yohimbinic acid monohydrate (CAS#27801-27-2), Menadione (CAS#58-27-5), Fluphenazine dihydrochloride (CAS#146-56-5), Trifluoperazine dihydrochloride (440-17-5). Piperacetazine (CAS#3819-00-9) was obtained directly from the Prestwick Small Molecule library resource. Rauwolscine hydrochloride (CAS#6211-32-1) was obtained from Santa Cruz Biotechnology, Inc.

MyoD Induction, Myotube Fusion, and AO Transfection iDRMs (inducible directly reprogrammable myotubes) were seeded at 150,000 cells per well in fibroblast growth media (DMEM (+phenol red, high glucose)+15% Fetal Bovine Serum (FBS)+1% Nonessential amino acids+1% pen/strep) in 6-well plates (Corning) pre-coated for 1 hour with 2.5 mL of 5 µg/mL laminin in serum free DMEM (BD Biosciences). The following day, 5 µM 4OH-tamoxifen (Sigma; resuspended in ethanol) was added in fibroblast growth media for 24 hours. On day 3, cells were washed in 1× Phosphate Buffered Saline (PBS; Invitrogen), and fusion media containing 1 µM 4OH-tamoxifen was added (1:1 Ham's F-10:DMEM (phenol red free, high glucose), 2% Horse Serum, 2% Insulin-Transferrin-Selenium). On Day 7, cells were transfected with 50 nM, 100 nM or 200 nM, 2-O-methyl AO targeting exon 51 (5'-UCAAGGAAGAUG-GCAUUUCU-3') (SEQ ID NO:2) (MWG Operon) using the ExGen500 (Fermentas) transfection reagent at a ratio of 5.5 µL:1 µg of DNA. AO was removed on day 8, cells were washed with 1×PBS, and fresh fusion media containing 1 µM 4OH-tamoxifen was added with titrating concentrations of drug and carrier controls. Forty-eight hours later, cell pellets were harvested and frozen for subsequent RNA isolation and exon skipping analysis [33].

A 5' FAM labeled 2'OMe AO targeting exon 51 (FAM-h51AON; 5'-FAM-UCAAGGAAGAUGGCAUUUCU-3', GenScript) (SEQ ID NO:3) was used for flow cytometry experiments assessing the efficiency of labeled AO uptake. FAM-h51AON was added on Day 7 to fusing iDRMs, removed, and cells were washed in 1×PBS. Forty-eight hours later each well was split in half; one half dedicated to RNA isolation and exon 51 skipping analysis, and the other half to flow cytometry analysis. For flow cytometry, cells were gated on the live population and the percentage of FAM positive cells was analyzed using WinMDI software.

RNA Isolation, PCR, and qPCR

Cell pellets were collected, and total RNA isolated using the QIAGEN RNeasy Microkit. For exon 51 skipping analysis, 200 ng of total RNA was reverse transcribed with an exon 54 gene specific primer [20]. A nested PCR was performed between DMD exons 43-52 using previously described primers, and the amplified product run on the Agilent 2100 Bioanalyzer for exon skipping quantification [20,33].

Example II. Results

Correlation Between AO Uptake and Exon Skipping Activity

We explored the relationship between antisense oligonucleotide uptake and how it correlates to exon skipping activity in a cell culture system. To do this we used a 5' FAM labeled 2'OMe AO so that cellular uptake could be directly measured by flow cytometry and then related to DMD exon 51 skipping activity in iDRM5017. After plating and seven days of fusion, FAM-h51AON was added to the cells for 24 hours after which it was removed. Forty-eight hours later each well was harvested and split for analysis; one half designated for analysis by flow cytometry and the other half analyzed for exon 51 skipping activity by RT-PCR and capillary electrophoresis. We found that there was a dose dependent increase in the percentage of FAM positive cells (FIG. 1a). At the highest doses of 200 nM and 300 nM of FAM-h51AON the proportion of positive cells was nearing 100% of the entire population, and was almost indistinguishable from the positive control, the nuclear dye Quinacrine dihydrochloride. This trend was consistently observed when looking at a different measure, the mean fluorescence intensity (MFI) (FIG. 1b).

Figure 8:
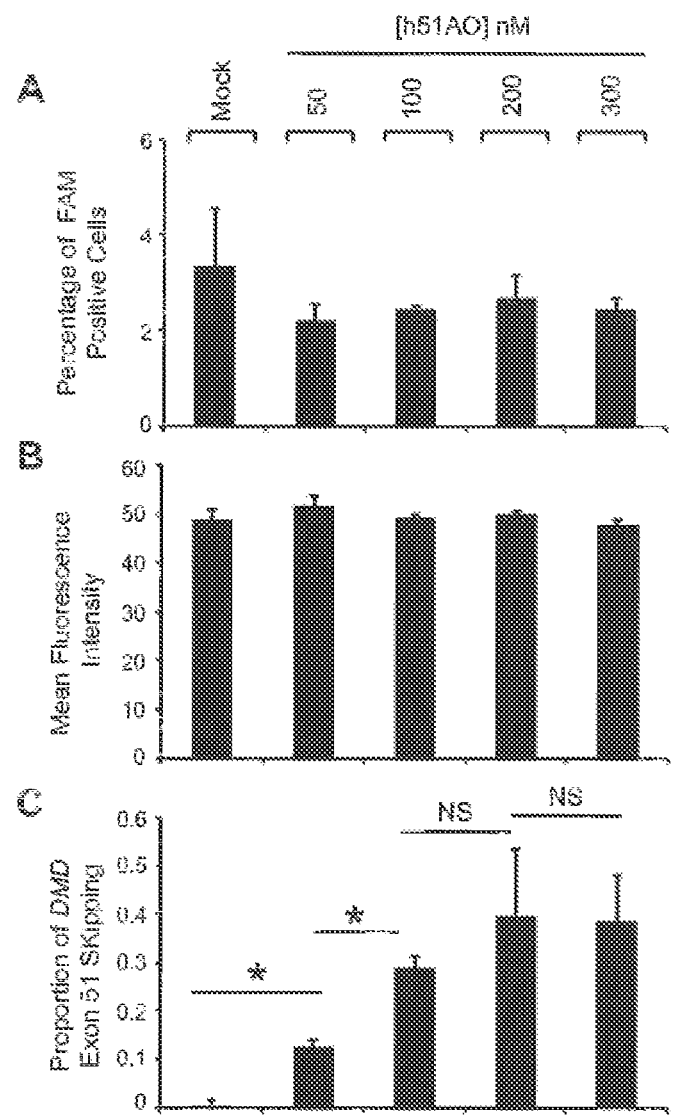
FIG. 8 shows unlabeled AO uptake and exon skipping activity in iDRM5017. This experiment was performed in parallel to the FAM labeled AO experiment presented in FIG. 1. On the seventh day of iDRM5017 fusion, h51AON targeting DMD exon 51 was transfected for 24 hours after which it was removed. After 48 hours each well was harvested for analysis, and split in half. (A) After gating on live cells, the percentage of FAM (or AO) positive cells was determined. (B) Mean fluorescence intensity of populations described in A. (C) The other half of each well was analyzed for DMD exon 51 skipping activity. Total RNA was isolated a nested RT-PCR performed between DMD exons 43-52. This experiment was repeated twice, with each condition being represented in triplicate. Error bars represent s.d. * indicates P<0.05. P values were determined using a two tailed student's t-test.

Although AO was added to cells with transfection reagent, the statistically significant increase in both FAM positive cells, and in the MFI, suggests that AO uptake was still to some extent dose dependent. From the conditions analyzed by flow cytometry we isolated total RNA and determined exon 51 skipping activity by a nested RT-PCR between DMD exons 43-52. There was a dose dependent increase in the proportion of DMD exon 51 skipping activity between 50-200 nM FAM-h51AON (FIG. 1c). However, at 300 nM FAM-h51AON there was a non-significant increase in the amount of observed exon skipping, indicating in this model a limitation of exon skipping capacity even with increased FAM-h51AON uptake (FIG. 1a, 1c). In parallel, an unlabeled h51AON 2'OMe was transfected into iDRM5017 and showed similar trends for DMD exon 51 skipping (FIG. 8). These data suggest that the identification of independent molecular targets could further facilitate exon skipping activity.

High Throughput Screen to Identify Small Molecule Enhancers of AO Mediated Exon Skipping To identify small molecules that synergize with antisense-based exon skipping strategies we performed a high-throughput screen of the Prestwick small molecule library (n=1120 compounds). We utilized an Exon50-GFP reporter construct that has been previously described in which skipping DMD exon 50 restores the GFP reading frame, resulting in fluorescence [32]. This construct was stably transfected into C2C12 cells, a mouse myoblast line, and plated on 384 well plate formats for small molecule screening at a 10 µM effective dose. Screens were performed in duplicate both in the presence of a sub-optimal dose of 300 nM 2'OMe h50AON antisense oligonucleotide directed against human exon 50 or with compounds only. AO was added before incubation of the cells with the small molecules to identify those that facilitate AO-mediated exon skipping rather than AO delivery. Fluorescence readouts were measured using an automated quantitative fluorescent scanning system.

Figure 9:
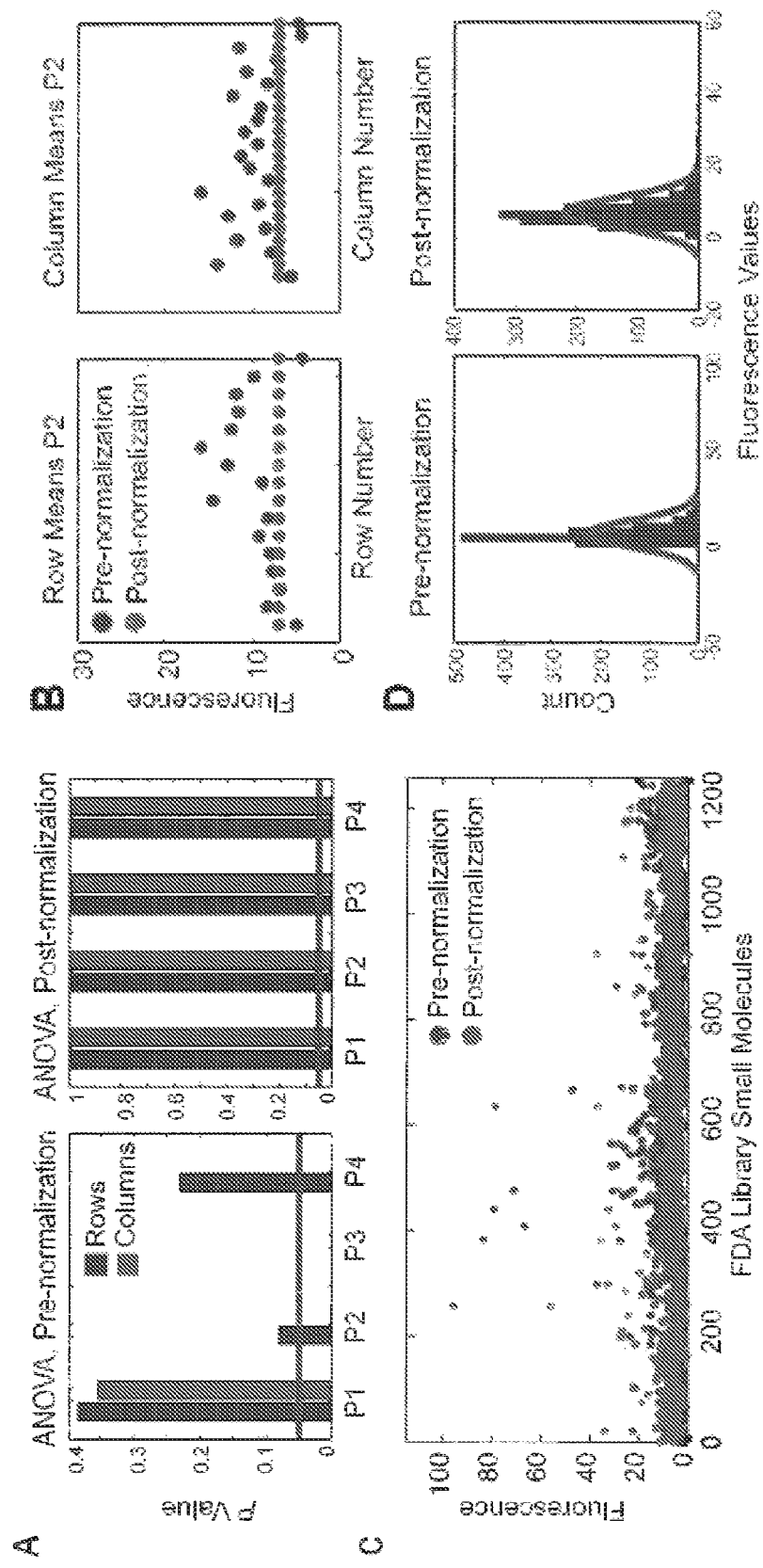
FIG. 9 shows normalization of high-throughput screening data. (A) Two-way ANOVA analysis of all Rows and Columns before and after fluorescence normalization for the 'Compound only' screen. P1-P4 indicates Plate 1, 2, 3, and 4. Blue represents fluorescence values before normalization and green represents fluorescence values after normalization. (B) Fluorescence values in the 'Compound only' screen for all Rows and Columns both before and after normalization for Plate 2 as an example. (C) Fluorescence values for all 1120 compounds both before and after normalization in the 'Compound only' screen. (D) Distribution of pre and post-normalized fluorescence values from the 'Compound only' screen. Red line indicates a normal distribution. (E) Panels E-H refer to the 'Compound+AO' analysis. Two-way ANOVA analysis of all Rows and Columns before and after fluorescence normalization in the 'Compound+AO' screen. P1-P4 indicates Plate 1, 2, 3, and 4. (F) Fluorescence values in the 'Compound+AO' screen for all Rows and Columns both before and after normalization for Plate 2 as an example. (G) Fluorescence values for all 1120 compounds both before and after normalization in the 'Compound+AO' screen. (H) Distribution of pre and post-normalized fluorescence values from the 'Compound+AO' screen. Red line indicates a normal distribution.
Figure 9:
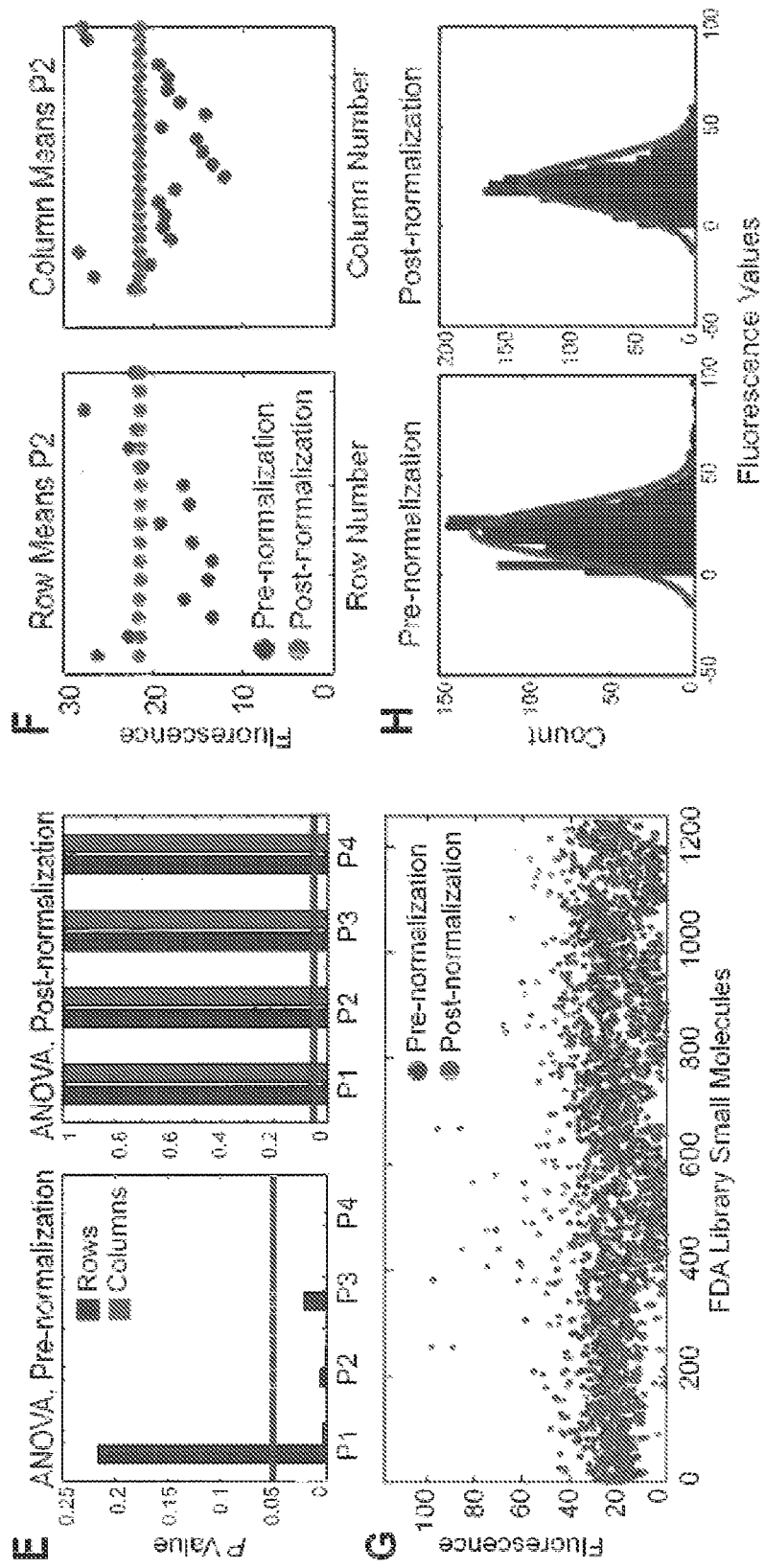

During analysis significant bias was observed between intra-plate row and column fluorescence values indicating the presence of systematic error (FIG. 9A, 9E) [42]. Therefore, fluorescence values from plate rows and columns were normalized by mean polish in a step-wise fashion, first on a plate-by-plate basis and then across plates, which significantly reduced the observed variability (Methods, Equations 1-2; FIG. 9B, 9F) [43]. Normalization was then performed across all four plates (Methods, Equations 3-4). Duplicate plates were normalized to each other to account for variability across screening days (FIG. 9C, 9G). This resulted in a better approximation of a normal distribution when comparing pre and post-normalization raw fluorescence values (FIG. 9D, 9H), as would be expected from an unbiased larger screen [43,44].

Figure 10:
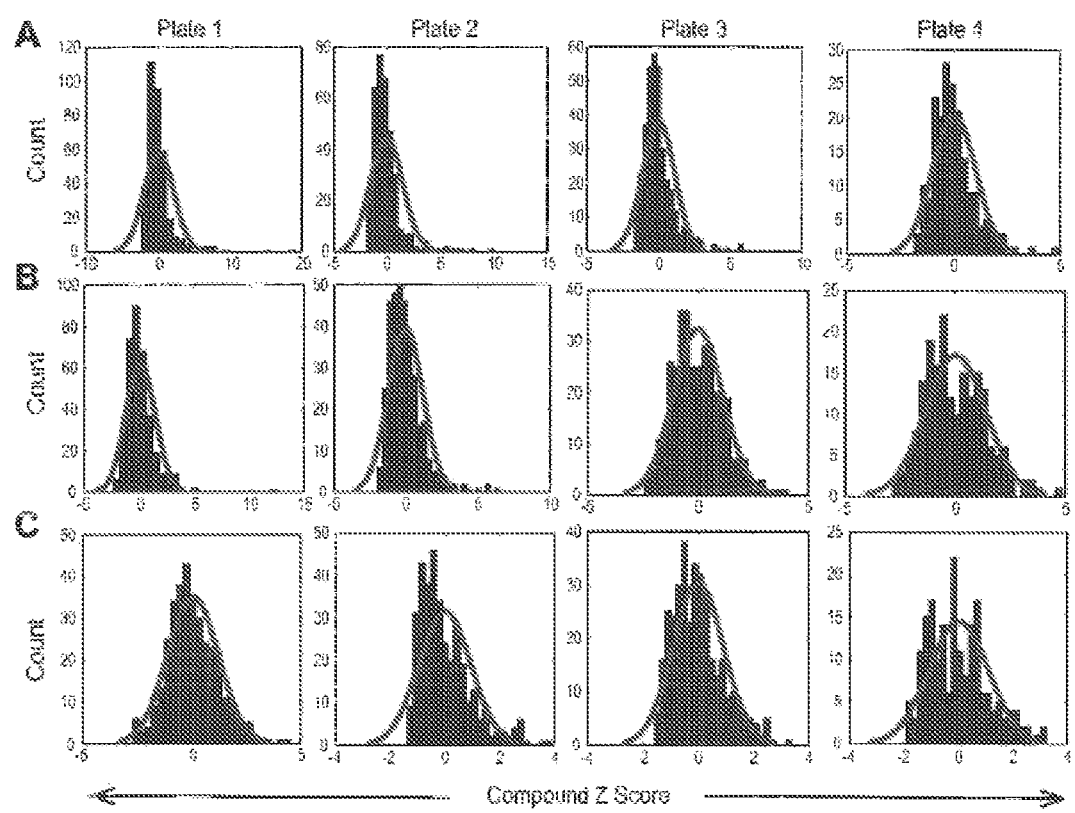
FIG. 10 shows that the distribution of Z scores is approximately normal. (A) 'Compound only' Z score analysis and their distributions across all four plates. Red line indicates a normal distribution. (B) 'Compound+AO' Z score analysis and their distributions across all four plates. Red line indicates a normal distribution. (C) Ratio of +AO/C Z score analysis and their distributions across all four plates. Red line indicates a normal distribution.

The Z score was calculated to differentiate compound performance in the screen, and represents the number of standard deviations away from the mean of the DMSO carrier controls (Methods, Equation 5). Z scores are plotted for all 1120 compounds in the 'without' and 'with AO' screen (FIG. 2a-b), with the distribution from each plate approximating normal (FIG. 10A-B). Both of these screens identified several small molecules that increased observed fluorescence (Table 1). To eliminate artifacts such as auto-fluorescent compounds (see arrow in FIG. 2a-b), and to better discriminate small molecules that only had activity in the 'Compound+AO' screen the ratio was calculated for the 'Compound+AO'/'Compound only' counterscreen (see Methods). The calculated ratio Z score is plotted for all 1120 compounds (FIG. 2c, FIG. 10C).

Figure 2:
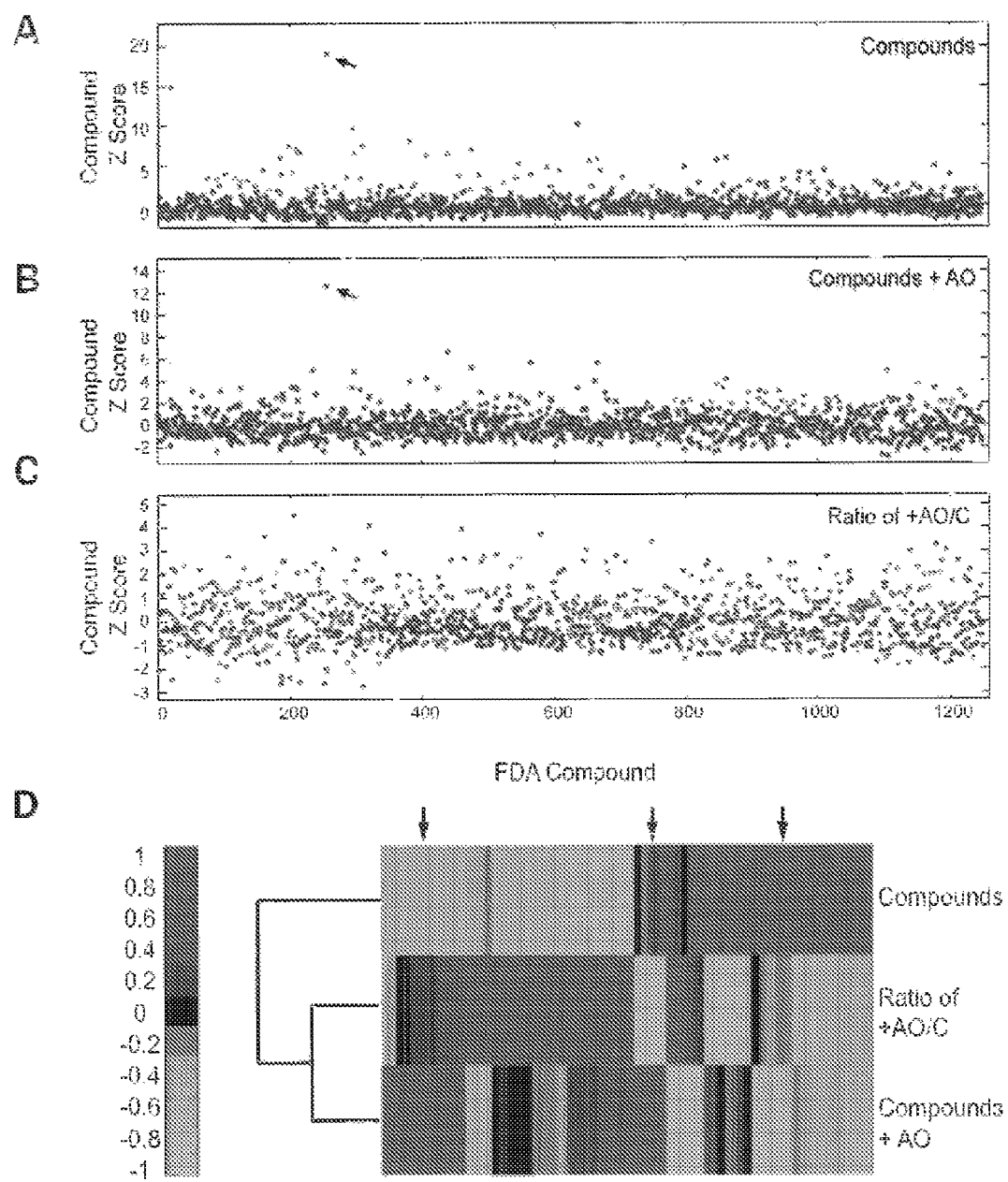
FIG. 2 shows high-throughput screening results and Z score determination. The Z score was calculated from normalized fluorescence values for (A) 'Compound only' screen (B) 'Compound+AO' screen, done in the presence of a sub-optimal h50AON dose and (C) the ratio of the 'Compound+AO' divided by the 'Compound only' screen (+AO/C). Arrows indicate a DNA intercalator, Quinacrine dihydrochloride that was eliminated in the +AO/C analysis. (D) Hierarchical clustering of Z score values for the three screens. Arrows indicate locations of compounds that were chosen for further evaluation; the left arrow represents Cluster 222, the middle arrow represents Cluster 394, and the right arrow represents Menadione.

This approach effectively eliminated the presence of false positives, such as Quinacrine Dihydrochloride, which is a DNA intercalator and emits in the same channel as GFP (FIG. 2a-c; Table 1). In principle, compounds with the highest ratio Z scores exhibit exon skipping activity specifically in the presence of AO. After hierarchical clustering analysis of all Z scores from all three screens, the ratio Z score had higher similarity to the 'with AO' screen, as would be expected (FIG. 2d).

TABLE 1

Z scores from the high-throughput screen for the 'Compound only' screen, 'Compound + AO' screen, and the analysis of the ratio of 'Compound + AO' compared to 'Compound only'.

| Rank | Chemical name | Z Score | CLSZ_0.65 | CLID_0.65 |
|---|---|---|---|---|
| | Table 1. Compound only. | | | |
| 1 | Quinacrine dihydrochloride dihydrate | 19.06 | 1 | 518 |
| 2 | Apomorphine hydrochloride hemihydrate | 14.87 | 1 | 28 |
| 3 | Menadione | 10.12 | 1 | 300 |
| 4 | Niclosamide | 9.59 | 1 | 317 |
| 5 | Methoxy-6-harmalan | 7.98 | 3 | 248 |
| 6 | Azaguanine-8 | 7.64 | 1 | 39 |
| 7 | Pyrimethamine | 7.44 | 1 | 400 |
| 8 | Fendiline hydrochloride | 7.39 | 2 | 449 |
| 9 | Albendazole | 7.00 | 2 | 540 |
| 10 | Ellipticine | 6.97 | 1 | 191 |
| 11 | Fenbendazole | 6.56 | 3 | 210 |
| 12 | Clotrimazole | 6.50 | 1 | 118 |
| 13 | Tetrahydroalstonine | 6.47 | 2 | 8 |
| 14 | Ajmalicine hydrochloride | 6.17 | 2 | 8 |
| 15 | Mefloquine hydrochloride | 5.92 | 1 | 429 |
| 16 | S(+)-Terguride | 5.92 | 3 | 418 |
| 17 | Harmaline hydrochloride dihydrate | 5.78 | 3 | 248 |
| 18 | Reserpine | 5.63 | 2 | 145 |
| 19 | Parthenolide | 5.51 | 1 | 717 |
| 20 | Daunorubicin hydrochloride | 5.14 | 2 | 185 |
| | Table 1. Compound + AO. | | | |
| 1 | Quinacrine dihydrochloride dihydrate | 12.60 | 1 | 518 |
| 2 | Tetrahydroalstonine | 6.56 | 2 | 8 |
| 3 | Rauwolscine hydrochloride | 5.62 | 4 | 394 |
| 4 | Harmaline hydrochloride dihydrate | 5.58 | 3 | 248 |
| 5 | Ellipticine | 5.17 | 1 | 191 |
| 6 | Oxethazaine | 4.98 | 1 | 620 |
| 7 | Reserpinic acid hydrochloride | 4.86 | 1 | 918 |
| 8 | Fenbendazole | 4.83 | 3 | 210 |
| 9 | Ajmalicine hydrochloride | 4.20 | 2 | 8 |
| 10 | S(+)-Terguride | 4.08 | 3 | 418 |
| 11 | Yohimbinic acid monohydrate | 3.95 | 4 | 394 |
| 12 | Methoxy-6-harmalan | 3.90 | 3 | 248 |
| 13 | Zardaverine | 3.69 | 1 | 285 |
| 14 | Reserpine | 3.66 | 2 | 145 |
| 15 | Meropenem | 3.56 | 1 | 1042 |
| 16 | Clemizole hydrochloride | 3.46 | 1 | 114 |
| 17 | Mebendazole | 3.43 | 3 | 210 |
| 18 | Econazole nitrate | 3.38 | 5 | 126 |

TABLE 1-continued

Z scores from the high-throughput screen for the 'Compound only' screen, 'Compound + AO' screen, and the analysis of the ratio of 'Compound + AO' compared to 'Compound only'.

| Rank | Chemical name | Z Score | CLSZ_0.65 | CLID_0.65 |
|---|---|---|---|---|
| 19 | Niclosamide | 3.37 | 1 | 317 |
| 20 | Piperacetazine | 3.35 | 6 | 222 |
| | Table 1. Ratio of +AO/C | | | |
| 1 | Clemizole hydrochloride | 4.49 | 1 | 114 |
| 2 | Fluphenazine dihydrochloride | 4.05 | 6 | 222 |
| 3 | Probucol | 3.92 | 1 | 343 |
| 4 | N6-methyladenosine | 3.70 | 3 | 309 |
| 5 | Isoflupredone acetate | 3.59 | 17 | 87 |
| 6 | Succinylsulfathiazole | 3.38 | 1 | 815 |
| 7 | Ondansetron Hydrochloride | 3.25 | 1 | 1059 |
| 8 | Metoclopramide monohydrochloride | 3.06 | 2 | 60 |
| 9 | Propoxycaine hydrochloride | 3.05 | 1 | 1082 |
| 10 | Sulfasalazine | 3.04 | 1 | 693 |
| 11 | Cefalonium | 2.97 | 1 | 995 |
| 12 | Methyldopa (L,-) | 2.84 | 2 | 182 |
| 13 | Hydroquinine hydrobromide hydrate | 2.82 | 4 | 65 |
| 14 | Tetramisole hydrochloride | 2.77 | 2 | 289 |
| 15 | Flumequine | 2.75 | 1 | 481 |
| 16 | Pipenzolate bromide | 2.74 | 3 | 69 |
| 17 | Procainamide hydrochloride | 2.67 | 2 | 422 |
| 18 | Tocopherol (R,S) | 2.67 | 1 | 520 |
| 19 | Phentolamine hydrochloride | 2.63 | 1 | 330 |
| 20 | Clemastine fumarate | 2.60 | 1 | 545 |

Figure 3:
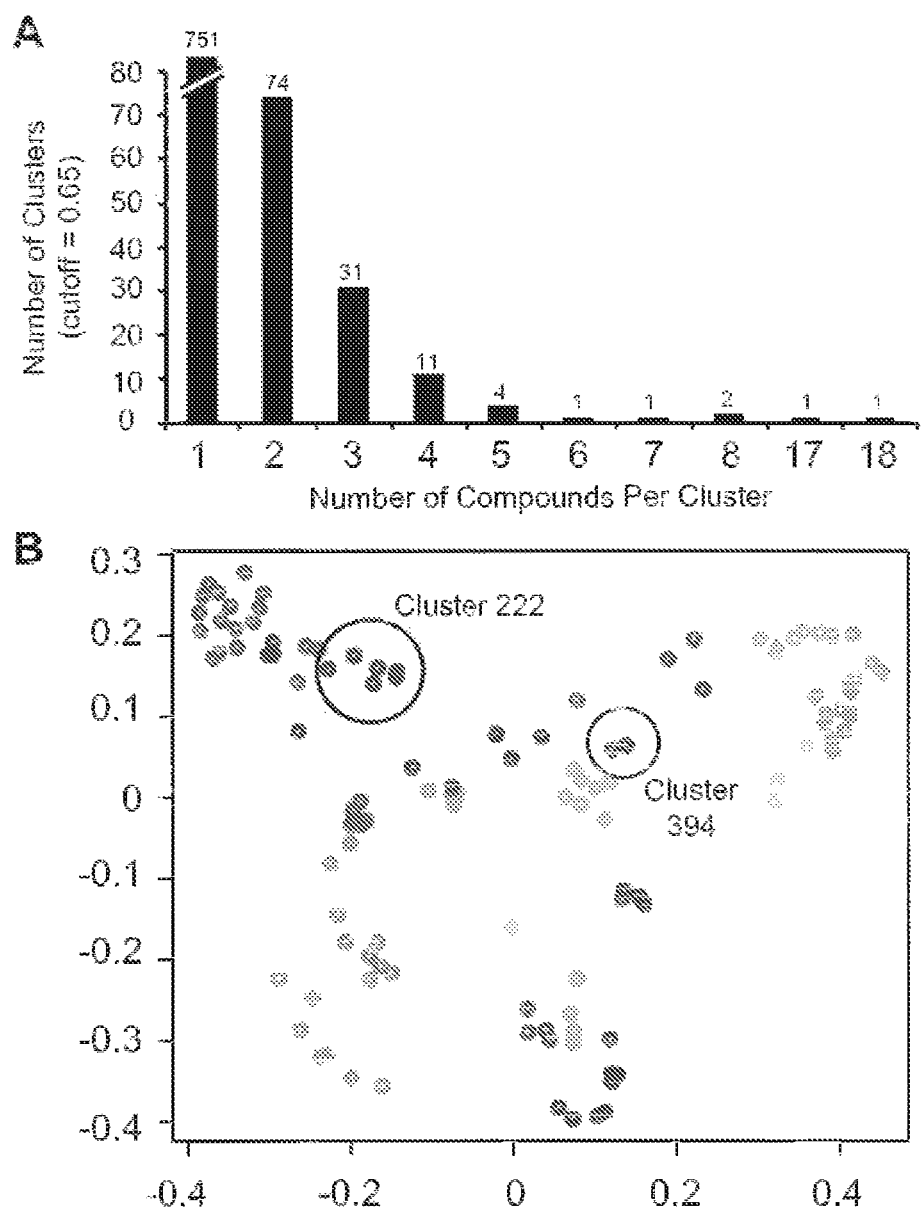
FIG. 3 shows 2-D structural clustering analysis of the Prestwick small molecule library. (A) Distribution of clusters present within the library as determined in ChemmineR. Similarity cutoff is 0.65. (B) Scatterplot of all of the clusters containing four or more compounds within the Prestwick small molecule library with a similarity cutoff of 0.65. Circled is Cluster 394 (n=4), which was identified from the 'Compound+AO' screen, as well as Cluster 222 (n=6), which was identified in the +AO/C ratio analysis.

Identification of Screening Hits by Combining 2-D Structural Clustering, Screen Performance, and Potential Molecular Targets We applied a 2-D structure-based clustering algorithm to the Prestwick library to determine if compounds with shared structural motifs exhibited comparable exon skipping activity [45]. The majority of compounds (n=751) did not have structurally similar counterparts. However, there were still multiple clusters of varying sizes ranging from 2-18 compounds (FIG. 3a). The structural similarity present in the library was plotted for all clusters containing four or more compounds, and circled clusters were chosen for additional evaluation in iDRMs (FIG. 3b). Shared structures would be expected to have similar binding partners, increasing the likelihood that an intersection of activity and targets will identify conserved pathways responsible for the observed exon skipping effect [45]. Therefore, we expanded the structural clustering analysis to include over 4,000 small molecule ligands present in the Protein Data Bank (PDB), which contains well-defined crystal structures of ligands bound to their respective protein targets, as an unbiased means to determine potential protein targets for our screen. We found many compounds that both performed well in the screen and were structurally similar to ligands identified in PDB (Table 2). Based on the PDB clustering results, exon skipping activity from the HTS, and the identification of additional compounds in the screen that possessed 2-D structural similarity, clusters of compounds were chosen for further evaluation in patient specific iDRMs.

TABLE 2

Compounds and their structurally similar ligands and protein targets identified from the Protein Data Bank.

| Compound Only | PDB Target |
|---|---|
| | Menadione (Screen Hit) |
| VK3 (PDB Ligand) | human quinone reductase type 2 |
| | Pyrimethamine |
| CP6 | plasmodium dihydrofolate reductase thymidylate synthase Daunorubicin hydrochloride |
| CMD | DNA |
| DM1 | DNA |
| DM2 | DNA |
| DM3 | DNA |
| DM5 | DNA |
| DM6 | DNA |
| DM7 | DNA |
| DM8 | DNA |
| DM9 | DNA |
| DMM | DNA |
| NOD | DNA |
| Compound + AO | PDB Target |
| | Zardaverine |
| ZAR | human phosphodiesterase 4d |
| Ratio of +AO/C | PDB Target |
| | Fluphenazine dihydrochloride |
| TFP | human calmodulin |
| | human troponin c |
| | N6-methyladenosine |
| 1DA | pre-transition state enzyme mimic; mouse adenosine deaminase |
| 3AD | yeast poly(a) polymerase |
| 9DI | bovine purine nucleoside phosphorylase |
| AD3 | trypanosoma vivax inosine-adenosine-guanosine-preferring nucleoside hydrolase |
| ADY | rattus S-adenosylhomocysteine hydrolase |
| | FM1, FM2, FMB e coli purine nucleoside phosphorylase |
| RPP | Isoflupredone acetate |
| AE2 | human dehydroepiandrosterone sulfotransferase |
| ANB | enterobacter pentaerythritol tetranitrate reductase |
| AND | brevibacterium cholesterol oxidase |
| | human dehydroepiandrosterone sulfotransferase |
| ANO | mouse Igg1-kappa db3 fab |
| AOM | human sex hormone-binding globulin |
| ASD | Saccharopolyspora Cytochrome p450eryf |
| | human estrogenic 17beta-hydroxysteroid dehydrogenase |
| DEX | human glucocorticoid receptor |

TABLE 2-continued

Compounds and their structurally similar ligands and protein targets identified from the Protein Data Bank.

| | |
|---|---|
| DHT | androgen receptor |
| PDN | corticosteroid-binding globulin |
| STR | human mineralocorticoid receptor |
| TES | androgen receptor |
| ZK5 | human androgen receptor |
| | Sulfasalazine |
| SAS | human glutathione s transferase |
| | Methyldopa (L,-) |
| DTY | yeast tyrosine-regulated 3-deoxy-d-arabino-heptulosonate-7-phosphate synthase |
| IPO | aeromonas proteolytica aminopeptidase |
| ISA | pig calpain |
| IYR | e coli tyrosyl-tryna synthetase |
| PHI | streptomyces griseus aminopeptidase |
| TPQ | pichia lysyl oxidase |
| | Tocopherol (R,S) |
| VIT | daboia phospholipase a2 |
| | human alpha-tocopherol transfer protein |

Assessment of Compound Synergy with AO in DMD Patient iDRMs

Figure 4:
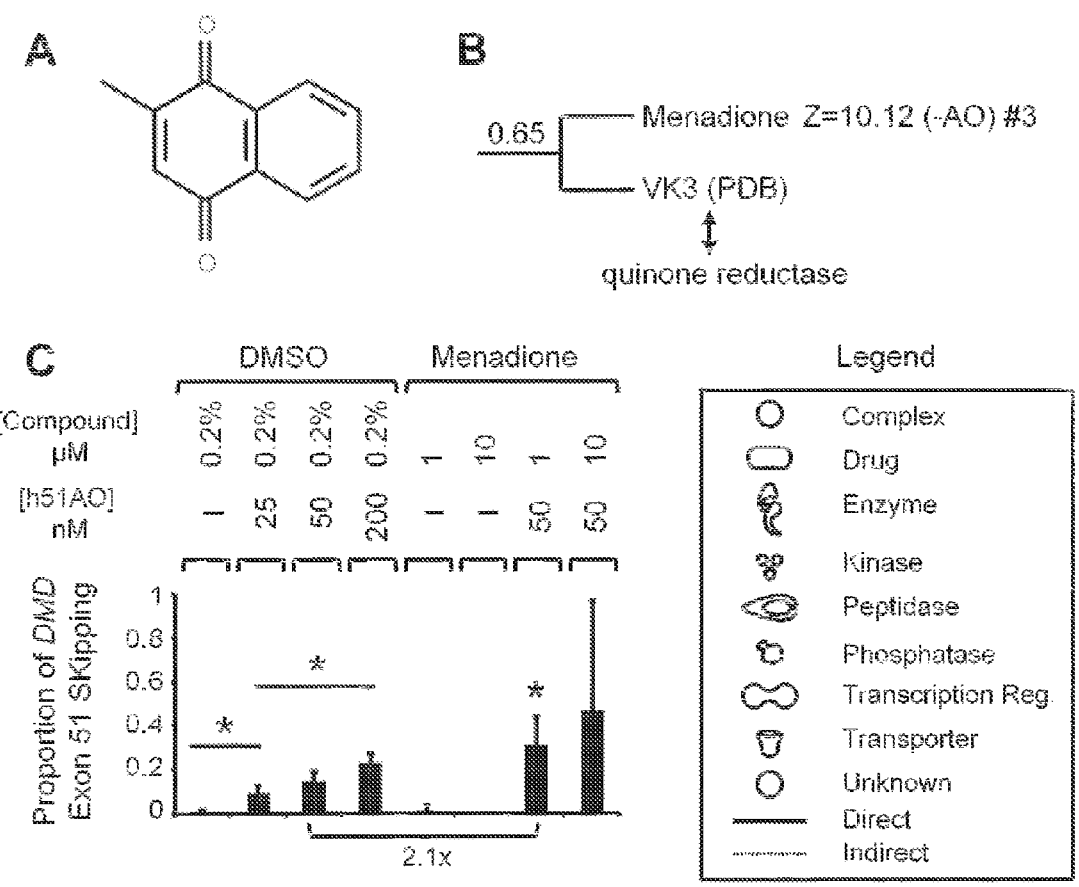
FIG. 4 shows Menadione as a potentiator of antisense-mediated exon skipping. Menadione was identified in the 'Compound only' screen. (A) Structure of Menadione, which (B) Clustered with VK3 in the Protein Data Bank, which has a known protein binding partner of quinone reductase. (C) Antisense-mediated DMD exon 51 skipping activity in iDRM5017. This experiment was repeated twice, with each condition being represented in triplicate. Error bars represent s.d. * indicates P<0.05. P values were determined using a two tailed student's t-test. (D) Ingenuity interaction map of all known Menadione direct (solid line) or indirect (dotted line) protein interactions.
Figure 4:
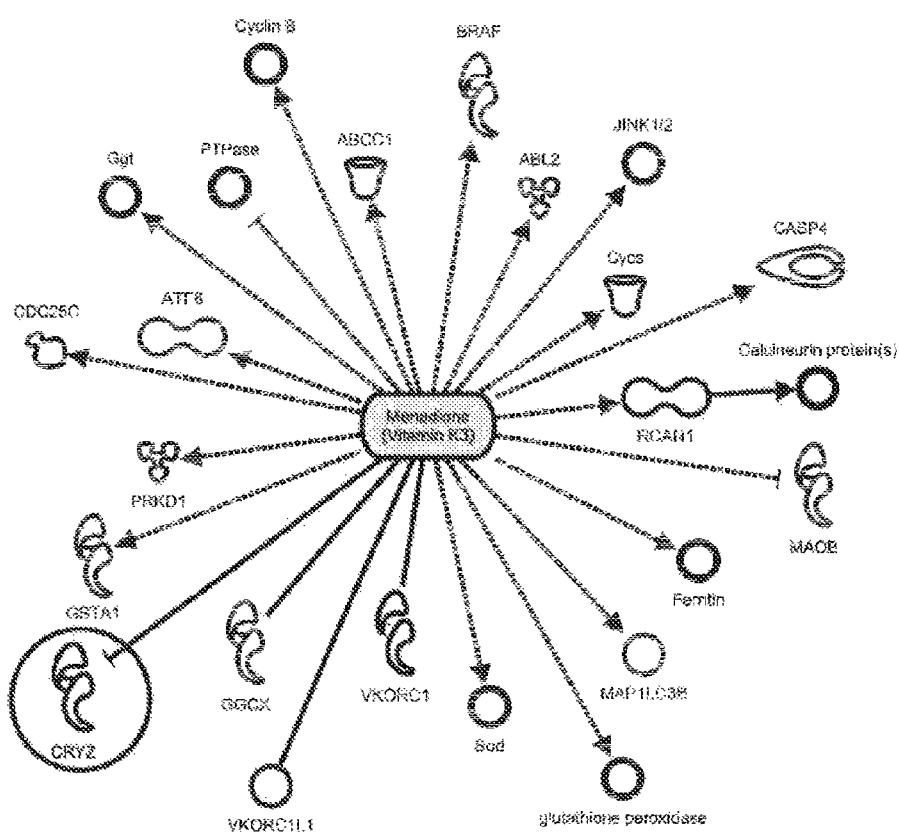

A subset of compounds was chosen to evaluate DMD exon skipping activity in iDRMs to determine if screening results were recapitulated in a relevant human model. iDRM5017 contains a DMD exon 45-50 deletion that is put back in-frame by the skipping of exon 51. Small molecules were assessed for synergy with doses of sub-optimal AO (50 nM) targeting exon 51. Representative compounds were chosen for evaluation from the 'Compound only' screen, the 'Compound+AO' screen, and the ratio analysis of the two screens. First, from the 'Compound only' screen, menadione was chosen based on its Z score rank (#3 overall) as well as clustering with a PDB molecular target, quinone reductase (Table 1, FIG. 4a-b). Previously, menadione was FDA approved as a dietary supplement. Menadione increased DMD exon 51 skipping moderately, approximately 2 fold at a 1 µM concentration in combination with the sub-optimal 50 nM h51AON dose (FIG. 4c). The 10 µM dose proved to be toxic to cells. In addition, menadione possesses potential molecular targets with downstream effects including those that menadione binds directly, such as quinone reductase, or targets in which expression is indirectly regulated (FIG. 4d).

Figure 5:
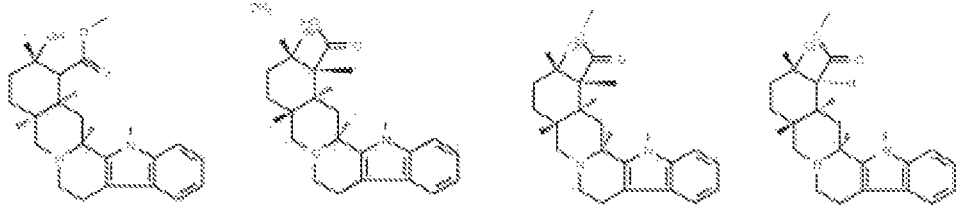
FIG. 5 shows that two structurally similar compounds from Cluster 394 increase antisense based exon skipping activity. Structurally similar cluster 394 was identified in the 'Compound+AO' screen, and consists of (A) Rauwolscine hydrochloride, Yohimbinic acid monohydrate, Yohimbine hydrochloride, and Corynanthine hydrochloride. (B) Hierarchical clustering of high-throughput screen performance for all four compounds. (C) DMD exon 51 skipping in iDRM5017. This experiment was repeated twice, with each condition being represented in triplicate. Error bars represent s.d. * indicates P<0.05. P values were determined using a two tailed student's t-test. (D) Ingenuity interaction map of all known cluster 394 direct or indirect protein interactions.
Figure 5:
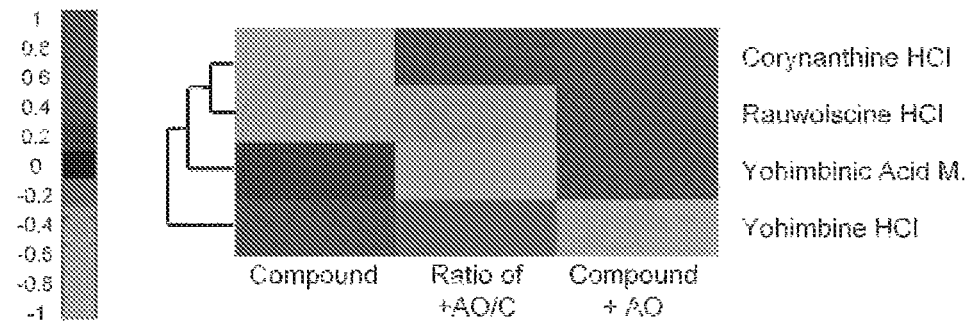
Figure 5:
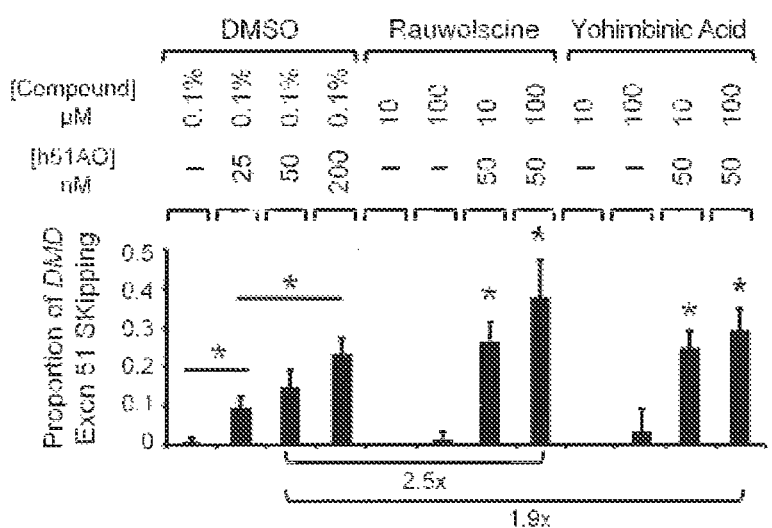
Figure 5:
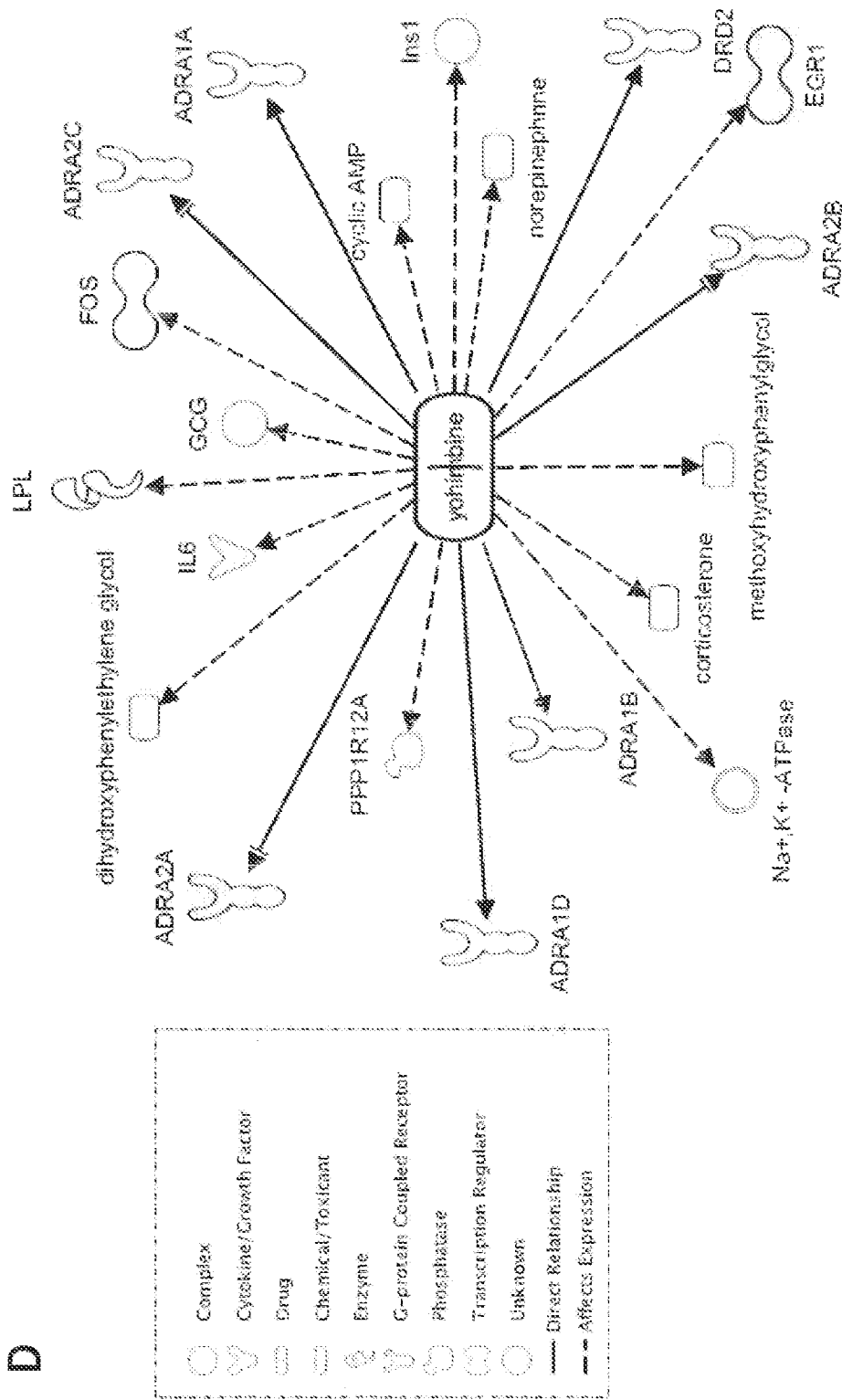

The subset of compounds chosen from the 'Compound+AO' screen was both highly ranked based on Z score and structurally similar. Cluster 394 was chosen based on these criteria and includes Rauwolscine hydrochloride (#3), Yohimbinic acid monohydrate (#11) and additional structurally similar compounds, Yohimbine hydrochloride and Corynanthine hydrochloride (Table 1, FIG. 5a). These plant alkaloids and FDA approved drugs are known to bind α1 and α2 adrenergic receptors and are currently used in the treatment of erectile dysfunction [46]. Based on hierarchical clustering of their screen performance, these compounds were predicted to possess similar exon skipping activity (FIG. 5b). Indeed, both Rauwolscine HCl and Yohimbinic Acid modestly increased DMD exon 51 skipping in iDRM5017 in a dose dependent manner, suggesting that they may be acting on a conserved molecular target (FIG. 5c). An analysis of their direct and indirect interactions includes an increase in expression of transcriptional regulators EGR1 and FOS, among other potential targets (FIG. 5d).

Figure 6:
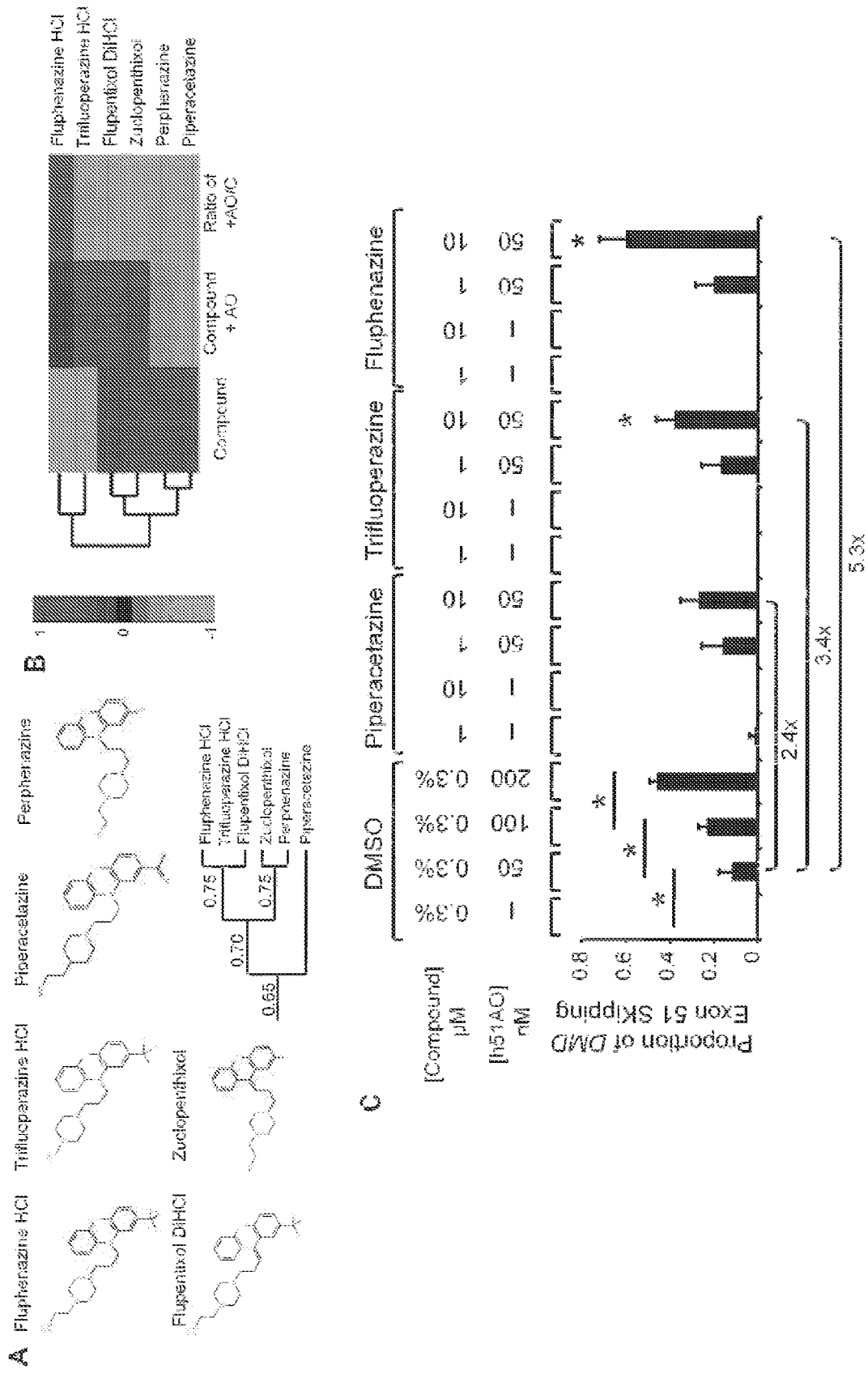
FIG. 6 shows that Cluster 222, a calmodulin binding partner, modulates AO targeted exon skipping. Structurally similar cluster 222 was identified in the 'ratio' analysis of high-throughput screening data and consists of (A) Fluphenazine hydrochloride, Trifluoperazine hydrochloride, Piperacetazine, Perphenazine, Flupentixol Dihydrochloride and Zuclopenthixol. To the right step-wise similarity cutoffs are displayed. (B) Hierarchical clustering of high-throughput screen performance for all compounds. (C) DMD exon 51 skipping in iDRM5017. This experiment was repeated twice, with each condition being represented in triplicate. Error bars represent s.d. * indicates P<0.05. P values were determined using a two tailed student's t-test.

Analysis of the ratio Z scores found a compound cluster that matched all three of these criteria: screen activity, structural similarity, and a putative molecular target from PDB. Cluster 222 is composed of phenothiazines that have been used in the treatment of psychiatric disorders, and includes 6 structurally similar small molecules, one of which, Fluphenazine dihydrochloride, was ranked #2 based on its Z score from the HTS (Table 1, FIG. 6a). All 6 compounds are structurally similar at a cut-off of 0.65; however, at more stringent cutoffs three groups are delineated one of which includes Fluphenazine and Trifluoperazine (TFP). Hierarchical clustering of screen performance indicates that Fluphenazine and Trifluoperazine are more closely related in terms of activity than the less structurally similar, Piperacetazine (FIG. 6b). These results were recapitulated when examining DMD exon 51 skipping in iDRM5017. Piperacetazine did not significantly increase antisense based exon skipping activity, which corroborates the high-throughput screening results. Trifluoperazine and Fluphenazine increase DMD exon 51 skipping in a dose dependent and statistically significant manner, ranging from a 3-5 fold increase (FIG. 6c), indicating that these structurally similar compounds have comparable exon skipping activity.

Figure 7:
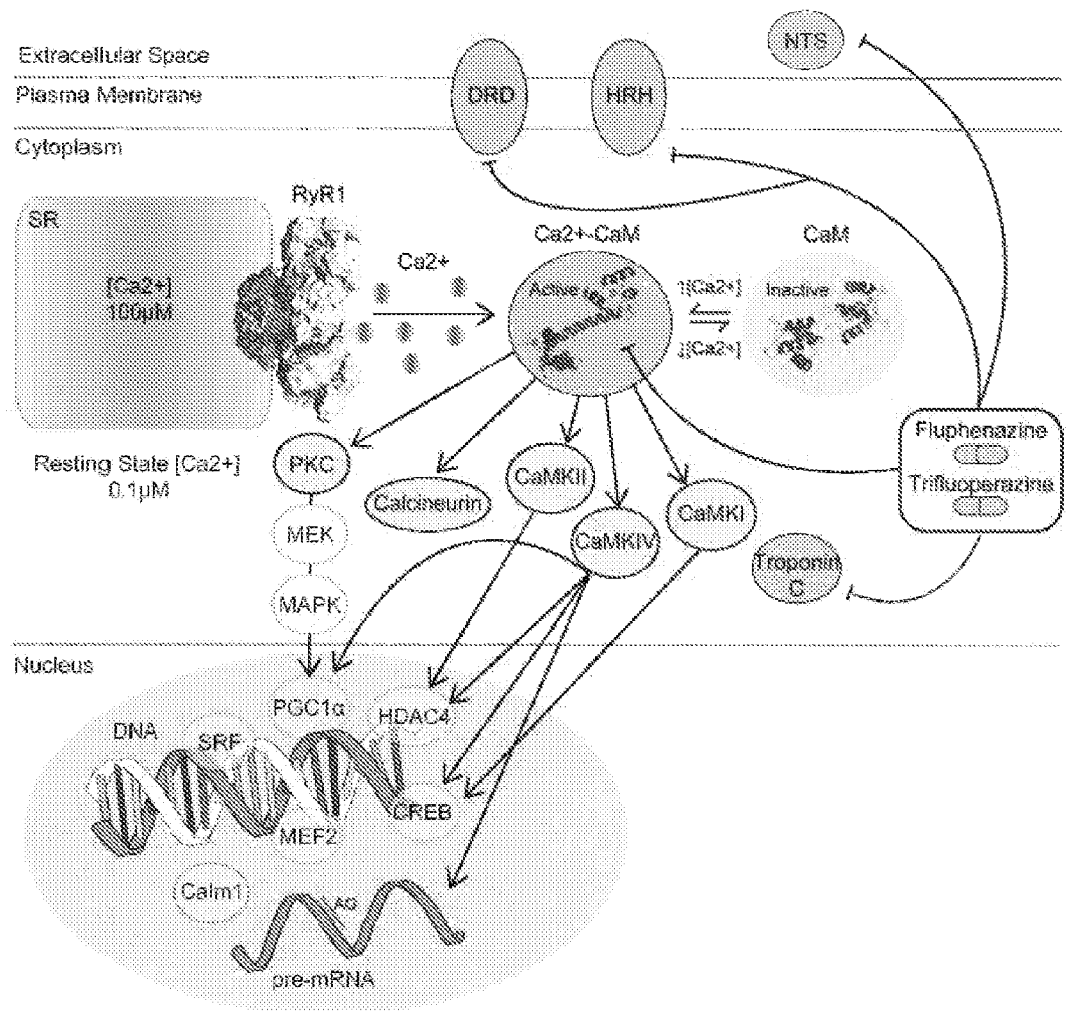
FIG. 7 shows a calcium mediated model of Cluster 222 directed exon skipping activity. Both Trifluoperazine and Fluphenazine exhibited an increase in exon skipping activity. All shared targets were determined by Ingenuity analysis and PDB analysis, and are displayed in their appropriate cellular compartments. Shared interactions between these two drugs and their direct and indirect affects are highlighted, as well as a sub-set of downstream signaling events that have been described in skeletal muscle.

Trifluoperazine and Fluphenazine share five molecular targets including dopamine receptors, histamine receptors, neurotensin, Troponin C, and Calmodulin (FIG. 7) [38,39]. Trifluoperazine is a PDB ligand with a crystal structure bound to CaM, a calcium secondary messenger that is well documented to regulate downstream transcriptional targets including MEF2, SRF, CREB, PGC-1α, among others [38, 39,47]. TFP potently binds Ca2+-CaM, or activated CaM, and this binding induces 3-D conformational changes from an active 'dumbbell' form to an inactive 'globular' form. In the inactive 'globular' form the CaM hydrophobic pockets are unavailable for binding by target proteins, suggesting that CaM inhibition may be the relevant activity for this exon skipping effect [38,39].

Example III—Discussion and Conclusions

DMD is one of the most common childhood forms of muscular dystrophy with no effective pharmacological therapies. Antisense oligonucleotides in clinical development target single exons for skipping, which restore the mRNA reading frame in a subset of DMD patients. To date, one of the main limitations with antisense based strategies is that the majority of systemically administered AO is cleared by the kidney instead of reaching the intended target, skeletal and cardiac muscle [48]. This has prompted studies focusing on improving AO efficacy, with strategies ranging from more efficient delivery methods to the identification of independent molecular targets [30-33]. Another possibility for the observed inefficiencies is that even with the highest doses of AO in cells, all DMD mRNA transcripts are not efficiently skipped. These limitations are not mutually exclusive, and both can be addressed by the identification of distinct molecular targets that enhance exon skipping activity either: 1) in the presence of a sub-optimal dose of AO or 2) to increase the amount of maximum exon skipping that is observed with AO alone.

Our strategy was to perform a HTS and determine small molecules and by extension their molecular targets that could potentiate AOs and increase DMD exon skipping activity. We found that structurally similar compounds increased exon 51 skipping in iDRM5017, with the most active exon skipping drugs deriving from the ratio Z score analysis. In addition, these compounds contained plausible molecular targets identified from PDB ligands. Applying 2-D structure analysis distinguished biologically active from inactive compounds and gave insight into integral molecular pathways [37].

Previous work has identified small molecules from HTS that increase AO targeted exon skipping. In 2009, O'Leary et al screened ~10,000 small molecules in combination with AO to identify those that enhance DMD exon 72 skipping via a construct expressed in HEK 293 cells, a non-muscle cell line [31]. In their strategy and set-up exon skipping is only observed in the presence of both drug and AO. Hu et al performed a HTS using the Ex50GFP reporter construct without the addition of AO, indicating that compounds may exhibit non-specific effects [32]. Our screen was performed in a muscle cell lineage with an Ex50GFP reporter construct both without and with a sub-optimal AO concentration that increased baseline fluorescence, where drug enhancement of AO activity was observed over that baseline. In addition, we included a counterscreen of compounds only, and the ratio Z score analysis identified compounds with potent exon skipping activity specific to AOs.

Compounds identified in the screen and chosen for further evaluation synergized with two AOs; one targeting exon 50 in the high-throughput screen, and h51AON targeting exon 51, indicating the mechanism of action is likely not dictated by AO sequence specificity. Additional investigation is expected to show that exon skipping is enhanced in other DMD mutations, with AOs targeting different exons, and that this trend is also observed with morpholino AOs. As noted above, small molecules of the invention, as well as other small molecules, target distinct proteins and signaling pathways, indicating that exon skipping activity can be further induced by a combinatorial strategy of more than two drugs. For example, recently a small molecule, Retro-1, was found to potentiate exon skipping at the level of intracellular trafficking or processing and is correlated with increased AO accumulation in the nucleus [49]. The combination of multiple compounds increases antisense efficacy.

Active drugs identified herein give insight into the link between affected molecular signaling pathways and how this translates into exon skipping. We identify Trifluoperazine and Fluphenazine as potent enhancers of AO exon skipping activity, with a well-documented molecular function of CaM inhibition [38,39]. CaM is the predominant cellular calcium sensor and is directly activated or inactivated by the concentration and spatiotemporal flux of calcium [50]. Typically, cytoplasmic Ca2+ concentrations are $10^3$ lower than Ca2+ concentrations in the sarcoplasmic reticulum (SR). In response to a rise in cytoplasmic Ca2+ concentrations, Ca2+-CaM will activate protein targets that redistribute from the cytosol to the nucleus and activate transcriptional targets or regulate alternative splicing processes [47,51,52]. Interestingly, O'Leary et al screened ~2000 kinase targeted siRNAs in a DMD exon 72 reporter construct, and found that knockdown of CaMK1 (a member of the Ca2+-Calmodulin dependent protein kinase family) and PKC, both downstream targets of CaM, increased AO targeted exon skipping 8 and 3 fold respectively, further supporting the observations described here [31].

Our previous work identified dantrolene inhibition of the RyR1 SR calcium channel, and modulation of intracellular calcium levels, as a mechanism for increasing AO exon skipping. Structurally distinct small molecule RyR1 inhibitors, ryanodine and S107, also increase AO based exon skipping, yet the mechanism by which RyR1 inhibition translates into exon skipping activity is unclear [53-55]. Trifluoperazine and Fluphenazine may provide insight into RyR1 downstream signaling events by indicating CaM as a relevant molecular target. Paradoxically, TFP has also been described in the activation of RyR2 mediated Ca2+ release (RyR receptor in cardiac muscle), a biological activity that is independent of its reported calmodulin inhibition [56]. This supports the hypotheses that either 1) RyR1 antagonists are acting in the same pathway, but upstream of TFP/Fluphenazine CaM inhibition or 2) RyR1 antagonists and TFP/Fluphenazine are acting on completely distinct targets. The events downstream of CaM activated alternative splicing remain to be understood, yet its potent inhibition can increase exon skipping 3-5 fold, suggesting the importance of Ca2+ regulation and its impact on Ca2+-binding proteins in directing exon skipping activity [38,39,53-55,57,58].

Without wishing to be bound by any particular mechanism, we propose a model in which dantrolene synergizes with AOs, regardless of sequence specificity and chemistry, to enhance targeted DMD exon skipping. This has been demonstrated both in vitro in mouse and human cell systems, as well as in multiple skeletal muscles with intramuscular and intravenous delivery of PMOE in the mdx mouse. Given the timing of addition of AO and drug, it is unlikely that dantrolene is enhancing uptake of AO. Without wishing to be bound by any particular mechanism, we suggest that it is enhancing exon skipping through interaction with a specific molecular target that is modulating DMD splicing activity. The concept of utilizing small molecules to increase exon skipping efficiency has been demonstrated in a patient with a rare point mutation in DMD exon 31 that disrupts an ESE binding site for the SRp30c splicing factor. The addition of TG003, a specific inhibitor for Clks known to phosphorylate SR proteins increased mutant exon 31 skipping and facilitated dystrophin protein rescue (Nishida et al (2011) *Nat Commun* 2, 308). However this therapeutic strategy is unlikely to be generalizable to broad treatment of DMD patients.

Without wishing to be bound by any particular mechanism, we propose that the mechanism by which dantrolene facilitates exon skipping may be that it functions by targeting the ryanodine receptor, its known molecular target. Ryanodine receptor regulates calcium release from the sarcoplasmic reticulum during excitation-contraction coupling in skeletal muscle. Because calcium signaling is a known regulator of splicing activity, dantrolene modulation of RyR1 mediated calcium flux in muscle is a plausible mechanism of its activity.

Studies of long-term dantrolene efficacy in the context of multiple AP injections and functional redouts, in the models presented herein as well as in humans, are expected to confirm the results presented herein, demonstrating that the optimized administration of the agents of the invention improves DMD disease progression.

REFERENCES

1. Mendell J R, Shilling C, Leslie N D, Flanigan K M, al-Dahhak R, et al. (2012) Evidence-based path to newborn screening for Duchenne muscular dystrophy. Ann Neurol 71: 304-313.
2. Hoffman E P, Brown R H, Jr., Kunkel L M (1987) Dystrophin: the protein product of the Duchenne muscular dystrophy locus. Cell 51: 919-928.
3. Bonilla E, Samitt C E, Miranda A F, Hays A P, Salviati G, et al. (1988) Duchenne muscular dystrophy: deficiency of dystrophin at the muscle cell surface. Cell 54: 447-452.
4. Petrof B J, Shrager J B, Stedman H H, Kelly A M, Sweeney H L (1993) Dystrophin protects the sarcolemma from stresses developed during muscle contraction. Proc Natl Acad Sci USA 90: 3710-3714.
5. Monaco A P, Bertelson C J, Middlesworth W, Colletti C A, Aldridge J, et al. (1985) Detection of deletions spanning the Duchenne muscular dystrophy locus using a tightly linked DNA segment. Nature 316: 842-845.
6. Charge S B, Rudnicki M A (2004) Cellular and molecular regulation of muscle regeneration. Physiol Rev 84: 209-238.
7. Jejurikar S S, Kuzon W M, Jr. (2003) Satellite cell depletion in degenerative skeletal muscle. Apoptosis 8: 573-578.
8. Vetrone S A, Montecino-Rodriguez E, Kudryashova E, Kramerova I, Hoffman E P, et al. (2009) Osteopontin promotes fibrosis in dystrophic mouse muscle by modulating immune cell subsets and intramuscular TGF-beta. J Clin Invest 119: 1583-1594.
9. Spencer M J, Tidball J G (2001) Do immune cells promote the pathology of dystrophin-deficient myopathies? Neuromuscul Disord 11: 556-564.
10. Leroy-Willig A, Willig T N, Henry-Feugeas M C, Frouin V, Marinier E, et al. (1997) Body composition determined with MR in patients with Duchenne muscular dystrophy, spinal muscular atrophy, and normal subjects. Magn Reson Imaging 15: 737-744.
11. Klingler W, Jurkat-Rott K, Lehmann-Horn F, Schleip R (2012) The role of fibrosis in Duchenne muscular dystrophy. Acta Myol 31: 184-195.
12. Kohler M, Clarenbach C F, Bahler C, Brack T, Russi E W, et al. (2009) Disability and survival in Duchenne muscular dystrophy. J Neurol Neurosurg Psychiatry 80: 320-325.
13. Ishikawa Y, Miura T, Ishikawa Y, Aoyagi T, Ogata H, et al. (2011) Duchenne muscular dystrophy: survival by cardio-respiratory interventions. Neuromuscul Disord 21: 47-51.
14. Biggar W D, Harris V A, Eliasoph L, Alman B (2006) Long-term benefits of deflazacort treatment for boys with Duchenne muscular dystrophy in their second decade. Neuromuscul Disord 16: 249-255.
15. Fenichel G M, Florence J M, Pestronk A, Mendell J R, Moxley R T, 3rd, et al. (1991) Long-term benefit from prednisone therapy in Duchenne muscular dystrophy. Neurology 41: 1874-1877.
16. Tinsley J, Deconinck N, Fisher R, Kahn D, Phelps S, et al. (1998) Expression of full-length utrophin prevents muscular dystrophy in mdx mice. Nat Med 4: 1441-1444.
17. Bowles D E, McPhee S W, Li C, Gray S J, Samulski J J, et al. (2012) Phase 1 gene therapy for Duchenne muscular dystrophy using a translational optimized AAV vector. Mol Ther 20: 443-455.
18. Price F D, Kuroda K, Rudnicki M A (2007) Stem cell based therapies to treat muscular dystrophy. Biochim Biophys Acta 1772: 272-283.
19. Welch E M, Barton E R, Zhuo J, Tomizawa Y, Friesen W J, et al. (2007) PTC124 targets genetic disorders caused by nonsense mutations. Nature 447: 87-91.
20. van Deutekom J C, Janson A A, Ginjaar I B, Frankhuizen W S, Aartsma-Rus A, et al. (2007) Local dystrophin restoration with antisense oligonucleotide PRO051. N Engl J Med 357: 2677-2686.
21. Goemans N M, Tulinius M, van den Akker J T, Burm B E, Ekhart P F, et al. (2011) Systemic administration of PRO051 in Duchenne's muscular dystrophy. N Engl J Med 364: 1513-1522.
22. Kinali M, Arechavala-Gomeza V, Feng L, Cirak S, Hunt D, et al. (2009) Local restoration of dystrophin expression with the morpholino oligomer AVI-4658 in Duchenne muscular dystrophy: a single-blind, placebo-controlled, dose-escalation, proof-of-concept study. Lancet Neurol 8: 918-928.
23. Cirak S, Arechavala-Gomeza V, Guglieri M, Feng L, Torelli S, et al. (2011) Exon skipping and dystrophin restoration in patients with Duchenne muscular dystrophy after systemic phosphorodiamidate morpholino oligomer treatment: an open-label, phase 2, dose-escalation study. Lancet 378: 595-605.
24. Aartsma-Rus A, Fokkema I, Verschuuren J, Ginjaar I, van Deutekom J, et al. (2009) Theoretic applicability of antisense-mediated exon skipping for Duchenne muscular dystrophy mutations. Hum Mutat 30: 293-299.
25. Mendell J R (2013) Results at 74 Weeks of a Phase IIb Extension Study of the Exon-Skipping Drug Eteplirsen in Patients with Duchenne Muscular Dystrophy (DMD). Muscular Dystrophy Association Scientific Conference. Washington D.C.
26. Anthony K, Cirak S, Torelli S, Tasca G, Feng L, et al. (2011) Dystrophin quantification and clinical correlations in Becker muscular dystrophy: implications for clinical trials. Brain 134: 3547-3559.
27. Neri M, Torelli S, Brown S, Ugo I, Sabatelli P, et al. (2007) Dystrophin levels as low as 30% are sufficient to avoid muscular dystrophy in the human. Neuromuscul Disord 17: 913-918.
28. Phelps S F, Hauser M A, Cole N M, Rafael J A, Hinkle R T, et al. (1995) Expression of full-length and truncated dystrophin mini-genes in transgenic mdx mice. Hum Mol Genet 4: 1251-1258.
29. Alter J, Lou F, Rabinowitz A, Yin H, Rosenfeld J, et al. (2006) Systemic delivery of morpholino oligonucleotide restores dystrophin expression bodywide and improves dystrophic pathology. Nat Med 12: 175-177.
30. Moulton H M, Moulton J D (2010) Morpholinos and their peptide conjugates: therapeutic promise and challenge for Duchenne muscular dystrophy. Biochim Biophys Acta 1798: 2296-2303.
31. O'Leary D A, Sharif O, Anderson P, Tu B, Welch G, et al. (2009) Identification of small molecule and genetic modulators of AON-induced dystrophin exon skipping by high-throughput screening. PLoS One 4: e8348.
32. Hu Y, Wu B, Zillmer A, Lu P, Benrashid E, et al. (2010) Guanine analogues enhance antisense oligonucleotide-induced exon skipping in dystrophin gene in vitro and in vivo. Mol Ther 18: 812-818.
33. Kendall G C, Mokhonova E I, Moran M, Sejbuk N E, Wang D W, et at (2012) Dantrolene enhances antisense-mediated exon skipping in human and mouse models of Duchenne muscular dystrophy. Sci Transl Med 4: 164ra160.
34. Brown R D, Martin Y C (1995) Use of Structure-Activity Data to Compare Structure-Based Clustering Methods and Descriptors for Use in Compound Selection. J Chem Inf Comput Sci 36: 572-584.
35. Noble M E, Endicott J A, Johnson L N (2004) Protein kinase inhibitors: insights into drug design from structure. Science 303: 1800-1805.
36. Johnson M A, Maggioria G M (1990) Concepts and Applications of Molecular Similarity. New York: John Wiley & Sons. 393 p.
37. Kubinyi H (1998) Similarity and Dissimilarity: A Medicinal Chemist's View. Perspectives in Drug Discovery and Design: 225-252.

38. Cook W J, Walter L J, Walter M R (1994) Drug binding by calmodulin: crystal structure of a calmodulin-trifluoperazine complex. Biochemistry 33: 15259-15265.
39. Vandonselaar M, Hickie R A, Quail J W, Delbaere L T (1994) Trifluoperazine-induced conformational change in Ca(2+)-calmodulin. Nat Struct Biol 1: 795-801.
40. Cao Y, Charisi A, Cheng L C, Jiang T, Girke T (2008) ChemmineR: a compound mining framework for R. Bioinformatics 24: 1733-1734.
41. Moors S L, Vos A M, Cummings M D, Van Vlijmen H, Ceulemans A (2011) Structure-based site of metabolism prediction for cytochrome P450.2D6. J Med Chem 54: 6098-6105.
42. Dragiev P, Nadon R, Makarenkov V (2011) Systematic error detection in experimental high-throughput screening. BMC Bioinformatics 12: 25.
43. Malo N, Hanley J A, Carlile G, Liu J, Pelletier J, et al. (2010) Experimental design and statistical methods for improved hit detection in high-throughput screening. J Biomol Screen 15: 990-1000.
44. Malo N, Hanley J A, Cerquozzi S, Pelletier J, Nadon R (2006) Statistical practice in high-throughput screening data analysis. Nat Biotechnol 24: 167-175.
45. Johnson M, Maggioria G (1990) Concepts and Applications of Molecular Similarity. New York: John Wiley & Sons.
46. Morales A (2000) Yohimbine in erectile dysfunction: the facts. Int J Impot Res 12 Suppl 1: S70-74.
47. Al-Shanti N, Stewart C E (2009) Ca2+/calmodulin-dependent transcriptional pathways: potential mediators of skeletal muscle growth and development. Biol Rev Camb Philos Soc 84: 637-652.
48. Lu Q L, Wu B (2012) Systemic delivery of antisense oligomer in animal models and its implications for treating DMD. Methods Mol Biol 867: 393-405.
49. Ming X, Carver K, Fisher M, Noel R, Cintrat J C, et al. (2013) The small molecule Retro-1 enhances the pharmacological actions of antisense and splice switching oligonucleotides. Nucleic Acids Res 41: 3673-3687.
50. Chin D, Means A R (2000) Calmodulin a prototypical calcium sensor. Trends Cell Biol 10: 322-328.
51. Luby-Phelps K, Hori M, Phelps J M, Won D (1995) Ca(2+)-regulated dynamic compartmentalization of calmodulin in living smooth muscle cells. J Biol Chem 270: 21532-21538.
52. Xie J, Black D L (2001) A CaMK IV responsive RNA element mediates depolarization-induced alternative splicing of ion channels. Nature 410: 936-939.
53. Bellinger A M, Reiken S, Carlson C, Mongillo M, Liu X, et al. (2009) Hypernitrosylated ryanodine receptor calcium release channels are leaky in dystrophic muscle. Nat Med 15: 325-330.
54. Kobayashi S, Bannister M L, Gangopadhyay J P, Hamada T, Parness J, et al. (2005) Dantrolene stabilizes domain interactions within the ryanodine receptor. J Biol Chem 280: 6580-6587.
55. Rousseau E, Smith J S, Meissner G (1987) Ryanodine modifies conductance and gating behavior of single Ca2+ release channel. Am J Physiol 253: C364-368.
56. Qin J, Zima A V, Porta M, Blatter L A, Fill M (2009) Trifluoperazine: a rynodine receptor agonist. Pflugers Arch 458: 643-651.
57. Andersson D C, Marks A R (2010) Fixing ryanodine receptor Ca leak—a novel therapeutic strategy for contractile failure in heart and skeletal muscle. Drug Discov Today Dis Mech 7: e151-e157.
58. Fill M, Copello J A (2002) Ryanodine receptor calcium release channels. Physiol Rev 82: 893-922.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application No. 61/884,671, filed Sep. 30, 2013, and in the figures are hereby incorporated in their entirety by reference, particularly with regard to the information for which they are cited.

We claim:

1. A method for enhancing exon skipping in a pre-mRNA from a muscle dystrophin (DMD) gene, comprising contacting a cell that expresses the pre-mRNA with a composition comprising (a) an agent that inhibits ryanodine receptor (RyR1) and (b) an agent that inhibits calmodulin (CaM) and, optionally, (c) an antisense oligonucleotide that can induce skipping in the pre-mRNA.

2. The method of claim 1, wherein the composition comprises the antisense oligonucleotide that can induce skipping in the pre-mRNA.

3. The method of claim 2, wherein the antisense oligonucleotide can induce skipping in exon 23, 44, 45, 50, 51, 52, and/or 53 of the DMD gene.

4. The method of claim 1, wherein the agent that inhibits the ryanodine receptor (RyR1) is at least one of dantrolene, ryanodine, or S107.

5. The method of claim 4, wherein the composition comprises the antisense oligonucleotide that can induce skipping in the pre-mRNA, wherein the antisense oligonucleotide can induce skipping in exon 23, 44, 45, 50, 51, 52, and/or 53 in the pre-mRNA of the DMD gene.

6. The method of claim 1, wherein the agent that inhibits calmodulin (CaM) is at least one of perphenazine, flupentixol diHCl, zuclopenthixol, corynanthine HCl, yohimbinic acid M, yohimbine HCl, rauwolscine HCl, fluphenazine, and/or trifluoperazine.

7. The method of claim 6, wherein the composition comprises the antisense oligonucleotide that can induce skipping in the pre-mRNA, wherein the antisense oligonucleotide can induce skipping in exon 23, 44, 45, 50, 51, 52, and/or 53 in the pre-mRNA of the DMD gene.

8. The method of claim 1, wherein the agent that inhibits calmodulin (CaM) is at least one of perphenazine, flupentixol diHCl, and/or zuclopenthixol.

9. The method of claim 8, wherein the composition comprises the antisense oligonucleotide that can induce skipping in the pre-mRNA, wherein the antisense oligonucleotide can induce skipping in exon 23, 44, 45, 50, 51, 52, and/or 53 in the pre-mRNA of the DMD gene.

10. The method of claim 1, wherein the agent that inhibits calmodulin (CaM) is at least one of corynanthine HCl and/or yohimbine HCl.

11. The method of claim 10, wherein the composition comprises the antisense oligonucleotide that can induce skipping in the pre-mRNA, wherein the antisense oligonucleotide can induce skipping in exon 23, 44, 45, 50, 51, 52, and/or 53 in the pre-mRNA of the DMD gene.

12. The method of claim 1, wherein the agent that inhibits calmodulin (CaM) is perphenazine.

13. The method of claim 1, wherein the agent that inhibits calmodulin (CaM) is flupentixol diHCl.

14. The method of claim 1, wherein the agent that inhibits calmodulin (CaM) is zuclopenthixol.

15. The method of claim 1, wherein the agent that inhibits calmodulin (CaM) is corynanthine HCl.

16. The method of claim 1, wherein the agent that inhibits calmodulin (CaM) is yohimbine HCl.

17. The method of claim 1, wherein the agent that inhibits the RyR1 is at least one of dantrolene, ryanodine, and/or S107, and the agent that inhibits CaM is at least one of perphenazine, flupentixol diHCl, zuclopenthixol, corynanthine HCl, yohimbinic acid M, yohimbine HCl, rauwolscine HCl, fluphenazine, and/or trifluoperazine.

18. The method of claim 17, wherein the agent that inhibits CaM is at least one of perphenazine, flupentixol diHCl, and/or zuclopenthixol.

19. The method of claim 17, wherein the agent that inhibits CaM is at least one of corynanthine HCl and/or yohimbine HCl.

20. The method of claim 3, wherein the agent that inhibits the RyR1 is at least one of dantrolene, ryanodine, and/or S107, and the agent that inhibits CaM is at least one of perphenazine, flupentixol diHCl, zuclopenthixol, corynanthine HCl, yohimbinic acid M, yohimbine HCl, rauwolscine HCl, fluphenazine, and/or trifluoperazine.

* * * * *